US010882885B2

(12) United States Patent
Wallace et al.

(10) Patent No.: US 10,882,885 B2
(45) Date of Patent: Jan. 5, 2021

(54) PEPTIDE-BASED SYNTHETIC MOLECULES AND SILICA NANOSTRUCTURES

(71) Applicant: Massachusetts Institute of Technology, Cambridge, MA (US)

(72) Inventors: Andrea Kimi Wallace, Cambridge, MA (US); Maiko Furubayashi, Cambridge, MA (US); Christopher A. Voigt, Belmont, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/897,257

(22) Filed: Feb. 15, 2018

(65) Prior Publication Data

US 2018/0244725 A1 Aug. 30, 2018

Related U.S. Application Data

(60) Provisional application No. 62/459,251, filed on Feb. 15, 2017.

(51) Int. Cl.

| | | |
|---|---|---|
| *C07K 7/08* | (2006.01) |
| *C08K 3/36* | (2006.01) |
| *C01B 33/12* | (2006.01) |
| *C01B 33/157* | (2006.01) |
| *C08L 77/04* | (2006.01) |
| *B82Y 30/00* | (2011.01) |

(52) U.S. Cl.
CPC .............. *C07K 7/08* (2013.01); *C01B 33/122* (2013.01); *C01B 33/157* (2013.01); *C08K 3/36* (2013.01); *C08L 77/04* (2013.01); *B82Y 30/00* (2013.01); *C08K 2201/011* (2013.01)

(58) Field of Classification Search
None
See application file for complete search history.

(56) References Cited

U.S. PATENT DOCUMENTS

| | | | |
|---|---|---|---|
| 4,703,020 A | 10/1987 | Nakano et al. | |
| 2007/0238808 A1 | 10/2007 | Goldberg et al. | |
| 2008/0293919 A1* | 11/2008 | Kaplan ............ | C07K 14/43518 530/356 |
| 2010/0173367 A1* | 7/2010 | Marner, II ........... | A61B 5/0084 435/106 |
| 2016/0096868 A1 | 4/2016 | Cha et al. | |

FOREIGN PATENT DOCUMENTS

| | | |
|---|---|---|
| EP | 1817257 A1 | 8/2007 |
| EP | 2762488 A2 | 8/2014 |
| WO | WO 2006/043285 A1 | 4/2006 |

OTHER PUBLICATIONS

Lechner et al. ("Exploring the effect of native and artificial peptide modifications on silaffin induced silica precipitation," Chem. Sci., 2012, 3, 3500) (Year: 2012).*
Seker et al. "Engineered Peptides for Nanohybrid Assemblies," Langmuir 2014, 30, 2137-2143 (Year: 2014).*
Pender et al. "Peptide-Mediated Formation of Single-Wall Carbon Nanotube Composites," Nano Letters 2006, 6, 40-44 (Year: 2006).*
Coyle et al. "A Cleavable Silica-Binding Affinity Tag for Rapid and Inexpensive Protein Purification," Biotechnol. Bioeng. 2014;111: 2019-2026 (Year: 2014).*
Nguyen et al. A protein-protein interaction in magnetosomes: TPR protein MamA interacts with an Mms6 protein, Biochem Biophys Rep. 2016;7:39-44 (Year: 2016).*
Uniprot entry for concentrative nucleoside transporter 1, downloaded May 5, 2020 (Year: 2020).*
Uniprot entry for sodium/nucleoside contransporter , downloaded May 5, 2020 (Year: 2020).*
[No Author Listed], THAOC_24272. UniProt. Nov. 28, 2012. 5 pages. Retrieved from: http://www.uniprot.org/uniprot/K0RQ67.
[No Author Listed], THAOC_37500. UniProt. Nov. 28, 2012. 5 pages. Retrieved from: http://www.uniprot.org/uniprot/K0QYB9.
Adams et al., Genetically Engineered Peptides for Inorganics: Study of an Unconstrained Bacterial Display Technology and Bulk Aluminum Alloy. Adv Mater. Sep. 6, 2013;25(33):4530-91.
Ahmad et al., Rapid Bioenabled Formation of Ferroelectric BaTiO3 at Room Temperature from an Aqueous Salt Solution at Near Neutral pH. J Am Chem Soc. Jan. 9, 2008;130(1):4-5. Epub Dec. 8, 2007.
Amemiya et al., Controlled formation of magnetite crystal by partial oxidation of ferrous hydroxide in the presence of recombinant magnetotactic bacterial protein Mms6. Biomaterials. Dec. 2007;28(35):5381-9. Epub Aug. 27, 2007.
Banerjee et al., Cu nanocrystal growth on peptide nanotubes by biomineralization: Size control of Cu nanocrystals by tuning peptide conformation. Proc Natl Acad Sci USA. Dec. 9, 2003;100(25):14678-82. Epub Nov. 25, 2003.
Bassindale et al., An improved phage display methodology for inorganic nanoparticle fabrication. Chem Commun. Jul. 28, 2007:2956-8. doi: 10.1039/b702650a.
Borg et al., Generation of Multishell Magnetic Hybrid Nanoparticles by Encapsulation of Genetically Engineered and Fluorescent Bacterial Magnetosomes with ZnO and SiO 2. Small. Sep. 2, 2015;11(33):4209-17. doi: 10.1002/smll.201500028. Epub Jun. 8, 2015.
Brutchey et al., Biocatalytic Synthesis of a Nanostructured and Crystalline Bimetallic Perovskite-like Barium Oxofluorotitanate at Low Temperature. J Am Chem Soc. Aug. 9, 2006;128(31):10288-94.
Buckley et al., The sol-gel preparation of silica gels. J Chem Ed. Jul. 1, 1994;71(7):599-602.
Castro et al., A primer to scaffold DNA origami. Nat Methods. Mar. 2011;8(3):221-9. doi: 10.1038/nmeth.1570.
Cha et al., Silicatein filaments and subunits from a marine sponge direct the polymerization of silica and silicones in vitro. Proc Natl Acad Sci USA. Jan. 19, 1999;96(2):361-5.

(Continued)

*Primary Examiner* — Christina Bradley
(74) *Attorney, Agent, or Firm* — Wolf, Greenfield & Sacks, P.C.

(57) ABSTRACT

Described herein are novel synthetic molecules, polymers, and compositions comprising silica-binding peptides, and their methods of production. Also described herein are methods of synthesizing structurally and chemically complex silica-based materials using the synthetic molecules, polymers, and compositions.

20 Claims, 11 Drawing Sheets

Specification includes a Sequence Listing.

(56) References Cited

OTHER PUBLICATIONS

Chen et al., The synthesis of hydroxyapatite with different crystallinities by controlling the concentration of recombinant CEMP1 for biological application. Mater Sci Eng C Mater Biot Appl. Feb. 2016;59:384-389. doi: 10.1016/j.msec.2015.10.029. Epub Oct. 22, 2015.
Clark et al., Engineering the Microfabrication of Layer-by-Layer Thin Films. Adv Mater. Dec. 1998;10(8):1515-9.
Della-Cioppa et al., Melanin Production in *Escherichia coli* from a Cloned Tyrosinase Gene. Biotechnology (N Y). Jul. 1980;8(7):634-8.
Dickerson et al., Identification and Design of Peptides for the Rapid, High-Yield Formation of Nanoparticulate TiO2 from Aqueous Solutions at Room Temperature. Chem Mater. May 25, 2008;20(4):1578-84.
Dickerson et al., Identification of peptides that promote the rapid precipitation of germania nanoparticle networks via use of a peptide display library. Chem Commun (Camb). Aug. 7, 2004;(15):1776-7. Epub Jun. 30, 2004.
Ding et al., Biomimetic Production of Silk-Like Recombinant Squid Sucker Ring Teeth Proteins. Biomacromolecules. Sep. 8, 2014;15(9):3278-89. doi: 10.1021/bm500670r. Epub Aug. 5, 2014.
Djalali et al., Au Nanocrystal Growth on Nanotubes Controlled by Conformations and Charges of Sequenced Peptide Templates. J Am Chem Soc. May 14, 2003;125(19):5873-9.
Filin et al., Some Aspects of Precious Opal Synthesis. Aus Gemmologist. 2002. 5 pages.
Flynn et al., Synthesis and organization of nanoscale II-VI semiconductor materials using evolved peptide specificity and viral capsid assembly. J Mater Chem. 2003;13(10):2414-21.
Golec et al., Novel ZnO-binding peptides obtained by the screening of a phage display peptide library. J Nanopart Res. Nov. 2012;14(11):1218, 6 pages. Epub Oct. 4, 2012.
Guerette et al., Nanoconfined β-Sheets Mechanically Reinforce the Supra-Biomolecular Network of Robust Squid Sucker Ring Teeth. ACS Nano. Jul. 22, 2014;8(7):7170-9.
Gungormus et al., Regulation of in vitro Calcium Phosphate Mineralization by Combinatorially Selected Hydroxyapatite-Binding Peptides. Biomacromolecules. Mar. 2008;9(3):966-73. doi: 10.1021/bm701037x. Epub Feb. 14, 2008.
Kang et al., Microbial Synthesis of CdS Nanocrystals in Genetically Engineered *E. coli*. Angew Chem Int Ed Engl. 2008;47(28):5186-9. doi: 10.1002/anie.200705806.
Kroger et al., Polycationic Peptides from Diatom Biosilica That Direct Silica Nanosphere Formation. Science. Nov. 5, 1999;286(5442):1129-32.
Kroger et al., Self-Assembly of Highly Phosphorylated Silaffins and Their Function in Biosilica Morphogenesis. Sci. Oct. 18, 2002;298(5593):584-6. doi: 10.1126/science.1076221. Epub Nov. 2002.
Lechner et al., Silaffins in Silica Biomineralization and Biomimetic Silica Precipitation. Mar Drugs. Aug. 19, 2015;13(8):5297-333. doi: 10.3390/md13085297.
Li et al., Selective in Vitro Effect of Peptides on Calcium Carbonate Crystallization. Cryst Growth Des. 2002;2(5):387-93. doi: 10.1021/cg0255467.

Naik et al., Peptide Templates for Nanoparticle Synthesis Derived from Polymerase Chain Reaction-Driven Phage Display. Adv Funct Mater. 2004;14(1):25-30.
Naik et al., Biomimetic synthesis and patterning of silver nanoparticles. Nat Mater. Nov. 2002;1(3):169-72.
Nam et al., Virus-Enabled Synthesis and Assembly of Nanowires for Lithium Ion Battery Electrodes. Science. May 12, 2006;312(5775):885-8. Epub Apr. 6, 2006.
Okochi et al., Screening of peptide with a high affinity for ZnO using spot-synthesized peptide arrays and computational analysis. Acta Biomater. Jun. 2010;6(6):2301-6. doi: 10.1016/j.actbio.2009.12.025. Epub Dec. 16, 2009.
Pappalardo et al., Copper(ii) and nickel(ii) binding modes in a histidine-containing model dodecapeptide. New J Chem. May 2002;26(5):593-600. doi: 10.1039/b110655d.
Perry et al., From biomineral to biomaterials: the role if biomolecule-mineral interactions. Biochem Soc Trans. Aug. 2009; 37:687-91.
Prince et al., Construction, Cloning, and Expression of Synthetic Genes Encoding Spider Dragline Silk. Biochemistry. Aug. 29, 1995;34(34):10879-85.
Roy et al., Identification of a Highly Specific Hydroxyapatite-binding Peptide using Phage Display. Adv Mater. May 19, 2008;20(10):1830-6.
Schweitzer et al., Melanin-covered nanoparticles for protection of bone marrow during radiation therapy of cancer. Int J Radiat Oncol Biol Phys. Dec. 1, 2010;78(5):1494-502. doi: 10.1016/j.ijrobp.2010.02.020. Epub Apr. 24, 2010.
Staniland et al., Crystallizing the function of the magnetosome membrane mineralization protein Mms6. Biochem Soc Trans. Jun. 15, 2019;44(3):883-90. doi: 10.1042/BST20160057. Epub Jun. 9, 2019.
Sumerel et al., Biocatalytically Templated Synthesis of Titanium Dioxide. Chem Mater. Dec. 1, 2003;15(25):4804-9. Epub Nov. 15, 2003.
Thai et al., Identification and characterization of Cu2O- and ZnO-binding polypeptides by *Escherichia coli* cell surface display: toward an understanding of metal oxide binding. Biotechnol Bioeng. Jul. 20, 2004;87(2):129-37.
Tsiveriotis et al., Studies on the interaction of histidyl containing peptides with palladium(II) and platinum(II) complex ions. Coord Chem Rev. 1999:171-84.
Umetsu et al., Bioassisted Room-Temperature Immobilization and Mineralization of Zinc Oxide—The Structural Ordering of ZnO Nanoparticles into a Flower-Type Morphology. Adv Mater. Nov. 2005;17(21):2571-5.
Wallace et al., Applying Synthetic Biology to Synthesize Functional Materials. AlChE Sites. 2017. 2 pages. Retrieved from: https://www.aiche.org/sbe/conferences/synthetic-biology-engineering-evolution-design-seed/2017/proceeding/paper/applying-synthetic-biology-synthesize-functional-materials.
Zafar et al., Functional Material Feature of Bombyx mori Silk Light vs. Heavy Chain Proteins. Biomacromolecules. Feb. 9, 2015;16(2):606-14. doi: 10.1021/bm501667j. Epub Jan. 20, 2015.
Zhang et al., Tuning the autophagy-inducing activity of lanthanide-based nanocrystals through specific surface-coating peptides. Nat Mater. Sep. 2012;11(9):817-26. doi: 10.1038/nmat3363. Epub Jul. 15, 2012.
Zuo et al., Aluminum- and mild steel-binding peptides from phage display. Appl Microbiol Biotechnol. Sep. 2005;68(4):505-9. Epub Oct. 26, 2005.

\* cited by examiner

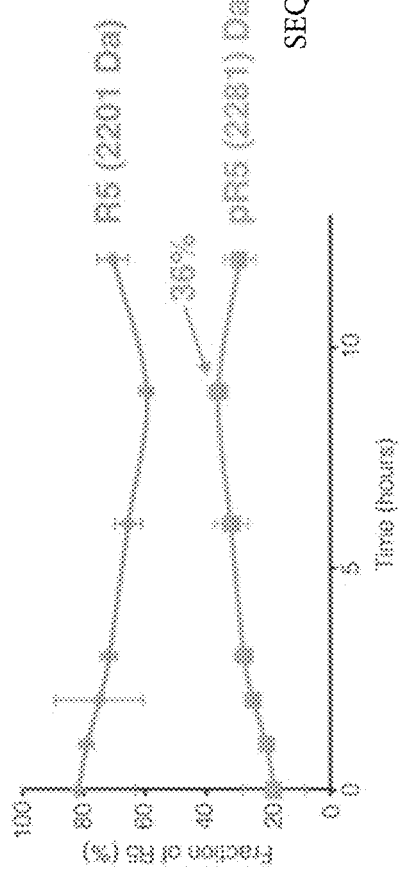

PEPTIDE-BASED SYNTHETIC MOLECULES AND SILICA NANOSTRUCTURES

RELATED APPLICATION

This application claims priority under 35 U.S.C. § 119(e) to U.S. provisional application No. 62/459,251, filed Feb. 15, 2017, which is incorporated herein by reference in its entirety.

GOVERNMENT SUPPORT

This invention was made with Government support under Grant No. HR0011-15-2-0033 awarded by the Defense Advanced Research Projects Agency, Grant No. N00014-15-1-0034 awarded by the Office of Naval Research, and Grant No. W911NF-09-D-0001 awarded by the Army Research Office. The Government has certain rights in the invention.

FIELD

Described herein are novel synthetic molecules, polymers, and compositions comprising silica-binding peptides, and their methods of production. Also described herein are methods of synthesizing structurally and chemically complex silica-based materials using the synthetic molecules, polymers, and compositions.

BACKGROUND

Advanced functional materials with highly organized nano- and microstructures are of increasing demand across the medical, optical, energy, and mechanical fields. Silica-based nano- and microstructures have potential use in a broad spectrum of applications; however, current methods of generated silica-based nano- and microstructures are limited. For example, previous attempts at encapsulating magnetosomes with silicate were performed by the sol-gel method in ~43% ethanol solvent, which is a harsh condition for the magnetosome membrane and proteins (Borg S., et al., Small, 2015 Sep. 2; 11(33): 4209-17). Other applications are limited by time and/or energy constraints. For example, typical methods of synthesizing synthetic opals can take up to a year and require high temperatures (Filin S. V., et al., Australian Gemmologist, 2002 January; 21: 278-282; U.S. Pat. No. 4,703,020; P.C.T. App. No. PCT/IN2005/000033). Likewise, previous methods of combining silica and melanin begin with pre-formed silica nanoparticles and require overnight reactions to coat the surfaces with melanin (Schweitzer A. D., et al., Int. J. Radiat. Oncol. Biol. Phys., 2010 Dec. 1; 78(5): 1494-1502).

SUMMARY

Advanced functional materials with highly organized nano- and microstructures are of increasing demand. The R5 peptide from the diatom *Cylindrotheca fusiformis* was previously shown to precipitate 500 nm diameter silica spheres in vitro (Kröger N., et al., Science, 1999 Nov. 5; 286(5442): 1129-32). However, the potential of the R5 peptide and other silica-binding peptides for generating highly organized nano- and microstructures has largely remained unexplored.

As demonstrated herein, synthetic molecules comprising silica-binding peptides, including R5 peptide, can be modified with post-translational modifications (PTMs) in vitro using modifying enzymes isolated from various organisms (both from diatoms and other organisms). Importantly, PTMs to silica-binding peptides can be used to control the morphology of precipitated silica, which can allow for the tunable control of silica structures required for various applications.

In some aspects the disclosure relates to synthetic molecules. In some embodiments, a synthetic molecule comprises or consists essentially of the amino acid sequence of a silica-binding peptide, wherein at least one amino acid of the silica-binding peptide contains at least one non-native post-translational modification. In some embodiments, the amino acid sequence of the silica-binding peptide comprises or consists essentially of the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, or a functional variant thereof.

In some embodiments, at least one of the at least one non-native post-translational modifications is selected from the group consisting of oxidation, phosphorylation, methylation, propylamination, myristoylation, hypusination, hydroxylation, adenylylation, biotinylation, lipidation, acetylation, glycosylation, propylamination, and sulfonation.

In some embodiments, the amino acid sequence of the silica-binding peptide consists essentially of SEQ ID NO: 1, wherein at least one amino acid of SEQ ID NO: 1 contains at least one non-native post-translational modification.

In some embodiments, at least one of the at least one non-native post-translational modifications is oxidation. In some embodiments, the oxidation occurs at Tyr10 of SEQ ID NO: 1.

In some embodiments, at least one of the at least one non-native post-translational modifications is phosphorylation. In some embodiments, the phosphorylation occurs at Ser1, Ser2, Ser5, Ser7, Ser9, Ser11 and/or Ser14 of SEQ ID NO: 1.

In some embodiments, at least one of the at least one non-native post-translational modifications is methylation. In some embodiments, the methylation occurs at Lys3, Lys4, Lys12, and/or Lys15 of SEQ ID NO: 1. In some embodiments, Lys3, Lys4, Lys12, and/or Lys15 of SEQ ID NO: 1 is methylated more than once.

In some embodiments, at least one of the at least one non-native post-translational modifications is propylamination. In some embodiments, the propylamination is the addition of spermine, spermidine, putrescine, and/or thermospermine to at least one amino acid of SEQ ID NO: 1.

In some embodiments, at least one of the at least one non-native post-translational modifications is myristoylation.

In some embodiments, at least one of the at least one non-native post-translational modifications is hypusination.

In some embodiments, at least two amino acids of the silica-binding peptide contain at least one non-native post-translational modification. In some embodiments, at least two of the at least two amino acids that have at least one non-native post-translational modification have the same non-native post-translational modification. In some embodiments, at least two of the at least two amino acids that have at least one non-native post-translational modification have a different non-native post-translational modification.

In some embodiments, the synthetic molecule comprises the amino acid sequence of a silica-binding peptide and at least one terminal fusion molecule, wherein each of the at least one terminal fusion molecules is fused to at least one terminal end of the amino acid sequence comprising the amino acid sequence of the silica-binding peptide.

In some embodiments, at least one of the at least one terminal fusion molecules is a biomolecule. In some embodiments, the biomolecule is a polypeptide. In some embodiments, the polypeptide is selected from the group consisting of Mms6, MamC, CNT1, and CNT2. In some embodiments, at least one of the at least one terminal fusion molecules is not a biomolecule.

In some embodiments, the amino acid sequence of the silica-binding peptide comprises the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, or SEQ ID NO: 34, and/or a functional variant, thereof.

In some embodiments, the at least one amino acid of the silica binding peptide contains at least one post-translational modification. In some embodiments, at least one of the at least one post-translational modifications is selected from the group consisting of oxidation, phosphorylation, methylation, propylamination, myristoylation, hypusination, hydroxylation, adenylylation, biotinylation, lipidation, acetylation, glycosylation, propylamination, and sulfonation.

In some embodiments, the amino acid sequence of the silica-binding peptide comprises an the amino acid sequence of SEQ ID NO: 1, wherein at least one amino acid of SEQ ID NO: 1 contains at least one post-translational modification.

In some embodiments, at least one of the at least one post-translational modifications is oxidation. In some embodiments, the oxidation occurs at Tyr10 of SEQ ID NO: 1.

In some embodiments, at least one of the at least one post-translational modifications is phosphorylation. In some embodiments, the phosphorylation occurs at Ser1, Ser2, Ser5, Ser7, Ser9, Ser11 and/or Ser14 of SEQ ID NO: 1.

In some embodiments, at least one of the at least one post-translational modifications is methylation. In some embodiments, the methylation occurs at Lys3, Lys4, Lys12, and/or Lys15 of SEQ ID NO: 1. In some embodiments, Lys3, Lys4, Lys12, and/or Lys15 of SEQ ID NO: 1 is methylated more than once.

In some embodiments, at least one of the at least one post-translational modifications is propylamination. In some embodiments, the propylamination is the addition of spermine, spermidine, putrescine, and/or thermospermine to at least one amino acid of SEQ ID NO: 1.

In some embodiments, at least one of the at least one post-translational modifications is myristoylation.

In some embodiments, at least one of the at least one post-translational modifications is hypusination.

In some embodiments, at least two amino acids of the silica-binding peptide contain at least one post-translational modification. In some embodiments, at least two of the at least two amino acids that have at least one post-translational modification have the same post-translational modification. In some embodiments, at least two of the at least two amino acids that have at least one post-translational modification have a different post-translational modification.

In some embodiments, a synthetic molecule comprises the amino acid sequence of a silica-binding peptide, wherein the amino acid sequence of the silica-binding peptide comprises the amino acid sequence of SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, or a functional variant thereof.

In some aspects the disclosure relates to polymers. In some embodiments, the polymer comprises a fusion of at least two synthetic molecules, wherein each of the at least two synthetic molecules is as described above. In some embodiments, at least two of the at least two synthetic molecules are chemically unique.

In some embodiments, the at least two synthetic molecules are fused through an interaction between at least one terminal end of each synthetic molecule. In some embodiments, the at least two synthetic molecules are fused through an interaction between at least one amino acid side chain of each synthetic molecule. In some embodiments, the polymer comprises R5-melanin.

In some aspects the disclosure relates to compositions. In some embodiments, a composition comprises at least one synthetic molecule, wherein each of the at least one synthetic molecules is as described above. In some embodiments, the composition comprises two or more types of synthetic molecules, wherein the two or more types of synthetic molecules are chemically unique.

In some embodiments, a composition comprises at least one polymer, wherein each of the at least one polymer is as described above. In some embodiments, the composition comprises two or more types of polymers, wherein the two or more types of polymers are chemically unique.

In some aspects the disclosure relates to methods of synthesizing a silica structure. In some embodiments, the method comprises contacting a synthetic molecule with a solution comprising dissolved silica, wherein the synthetic molecule is as described above.

In some embodiments, the synthetic molecule and the solution comprising dissolved silica are contacted at ambient temperature.

In some embodiments, the dissolved silica is aqueous silicic acid. In some embodiments, the dissolved silica is colloidal silica.

In some embodiments, the method also comprises contacting the synthetic molecule and the solution comprising dissolved silica with at least one metal nanoparticle. In some embodiments, at least one of the at least one metal nanoparticles is selected from the group consisting of an iron oxide nanoparticle, a zinc oxide nanoparticle, tantalum oxide nanoparticles, a hafnium oxide nanoparticle, a titanium oxide nanoparticle, a cadmium sulfide nanoparticle, a germanium oxide nanoparticle, an indium phosphide, and a cadmium selenide nanoparticle.

In some embodiments, the method also comprises contacting the synthetic molecule and the solution comprising dissolved silica with magnetosomes.

In some embodiments, the method also comprises contacting the synthetic molecule and the solution comprising dissolved silica with a biomolecule. In some embodiments, the biomolecule is DNA.

In some aspects, the disclosure relates to a melanin embedded silica structure generated by the method as described above.

In some aspects, the disclosure relates to an R5-Mms6 iron oxide nanoparticle silica structure as generated by the method as described above.

In some aspects, the disclosure relates to an R5-mamC magnetosome silica structure generated by the method as described above.

In some aspects, the disclosure relates to a carbon-nanotube-binding magnetosome silica structure generated by the method as described above.

In some aspects, the disclosure relates to a silica coated DNA-nanostructure generated by the method as described above.

In some aspects, the disclosure relates to an opal silica structure generated by the method as described above.

In some aspects, the disclosure relates to silica structures comprising precipitated silica and at least one synthetic molecule, wherein each of the at least one synthetic molecule is as described above.

In some embodiments, the silica structure also comprises iron oxide nanoparticles, wherein at least one of the at least one synthetic molecules is R5-Mms6.

In some embodiments, the silica structure also comprises magnetosomes. In some embodiments, at least one of the at least one synthetic molecules is R5-MamC. In some embodiments, at least one of the at least one synthetic molecules is R5-CNT. In some embodiments, the R5-CNT is R5-CNT1. In some embodiments, the R5-CNT is R5-CNT2.

In some embodiments, the silica structure also comprises a biomolecule. In some embodiments, the biomolecule is DNA.

In some aspects, the disclosure relates to silica structures comprising precipitated silica and at least one polymer, wherein each of the at least on polymer is as described above.

In some embodiments, at least one of the at least one polymers comprises R5-melanin.

In some aspects, the disclosure relates to a silica coated DNA-nanostructure comprising precipitated silica, R5 peptide, and DNA.

In some aspects, the disclosure relates to a methods of synthesizing a silica coated DNA-nanostructure. In some embodiments, the method comprises contacting DNA with R5 peptide and subsequently contacting the DNA and R5 peptide with a solution comprising dissolved silica. In some embodiments, the DNA and the R5 are contacted with the solution comprising dissolved silica at ambient temperature. In some embodiments, the dissolved silica is aqueous silicic acid. In some embodiments, the dissolved silica is colloidal silica.

These and other aspects of the invention are further described below.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. It is to be understood that the data illustrated in the drawings in no way limit the scope of the disclosure.

FIGS. 1A-1C. Phosphorylation of R5 by Protein Kinase A. FIG. 1A. The relative percentages of each R5 species (unmodified R5 and R5 modified with phosphate) over time. FIG. 1B. Increasing the ratio of PKA to R5 increases the proportion of phosphorylated R5 (ratios that converted up to 66% of R5 were tested). FIG. 1C. Manually assembled MS/MS fragmentation alignments. Targeted MS/MS analysis was performed on an Agilent QQQ, and data were interpreted manually. Each graph represents the fragments that were identified by specifically targeting the known mass of R5 with zero, one, or two phosphates added and detecting all product ions. Fragments were aligned to the region of R5 that the product ion mass corresponds to. Regions with increased height represent more fragment coverage. Fragments containing no phosphate mass shift are shown in dark shade, a mass shift corresponding to the presence of one phosphate are shown in medium shade, and with two phosphates are shown in light shade. Data indicated that the primary phosphorylation site was at Ser11, with very low levels of phosphorylation at Ser4, Ser7, and Ser16.

FIG. 2A. A heatmap showing the relative percentages of each R5 species (containing zero through 16 methyl groups) over time for wild-type SET7/9 and SET7/9 Y305F. FIGS. 2B-2C. Profile traces for zero through four methyl groups added to R5 over time for wild-type SET7/9 (FIG. 2B) and SET7/9 Y305F (FIG. 2C).

FIG. 3A. A heatmap showing the relative percentages of each R5 species (containing zero through 16 methyl groups) over time. FIG. 3B. Profile traces for zero through five methyl groups added to R5 over time. FIG. 3C. A schematic indicating which lysine residues are methylated over time. MS/MS analysis was performed on an Agilent QQQ and data were interpreted manually. Solid lines represent potential immediate connections between methylated states over time, while dashed lines represent potential connections that skip one or more intermediate states. Further MS/MS analysis on a Thermo Orbitrap was performed and data were analyzed computationally using MASCOT. All data indicated that methylation occurs on all four lysines with no discernable preference or pattern.

FIG. 4A. A heatmap showing the relative percentages of each R5 species (containing zero through 16 methyl groups) over time. FIG. 4B. Profile traces for zero through four methyl groups added to R5 over time.

FIG. 6A. Enzymatic oxidation of tyrosine by Tyrosinase leads to spontaneous formation of melanins. FIG. 6B. Within one hour a color change is observed. FIG. 6C. Spectroscopy indicates formation of melanin over time (peak at 350 nm). FIG. 6D. SDS-PAGE and Coomassie stain indicated polymerization of R5 peptides in the presence of Tyrosinase.

FIG. 10A. Iron oxide nanoparticles were synthesized in vitro by the partial oxidation method using R5-Mms6 (della-Cioppa G., et al., Biotechnology, 1990 July; 8(7): 634-38). FIG. 10B. Iron oxide nanoparticles were visualized by scanning electron microscopy (SEM) and transmission electron microscopy (TEM). Energy-dispersive X-ray spectroscopy (EDS) showed that all nanoparticles (first column) were composed of iron oxide ($Fe_3O_4$), and with the addition of TMOS, R5-Mms6-iron oxide nanoparticles (middle row, second column) were 87.4% $Fe_3O_4$ and 5.8% silica ($SiO_2$).

FIGS. 11A-11B. In the presence of TMOS and Ludox silicic acids, both wild-type magnetosomes (FIG. 11A) and R5-displaying magnetosomes (FIG. 11B) containing all coat proteins showed no statistical difference in their ability to precipitate layers of silica, even when additional R5 was doped into the reaction. FIGS. 11C-11D. However, when the MamA coat protein is removed with a solvent wash, R5-displaying magnetosomes showed an increased silica coating thickness when TMOS is the silica source and additional R5 is doped into the reaction. In the presence of Ludox silicic acid, wild-type magnetosomes without the MamA coat protein did not form silica coatings (FIG. 11C), while R5-displaying magnetosomes without MamA continued to show high propensity for becoming coated (FIG. 11D).

DETAILED DESCRIPTION

Figure 2A:
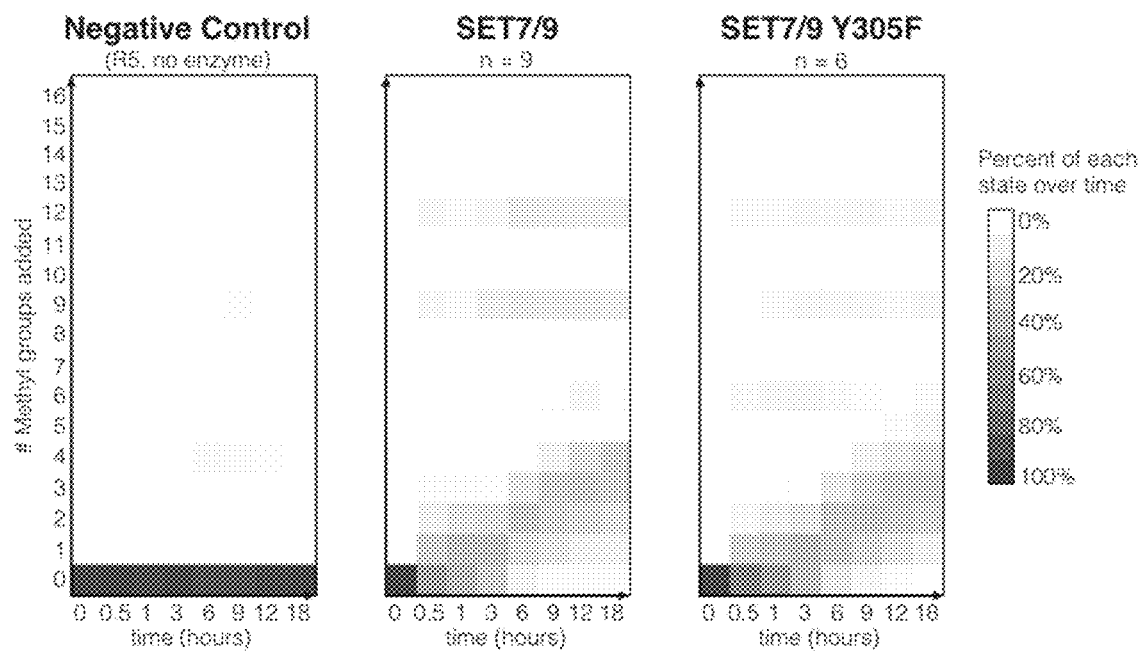
FIGS. 2A-2C. Methylation of R5 by Lysine Methyltransferase SETD7.

Advanced functional materials with highly organized nano- and microstructures are of increasing demand across the medical, optical, energy, and mechanical fields. Silica-based nano- and microstructures have potential use in a broad spectrum of applications; however, current technologies for generated silica-based nano- and microstructures are limited.

As demonstrated herein, silica-binding peptides, including R5 peptide, can be modified with post-translational modifications (PTMs) in vitro using modifying enzymes isolated from various organisms (both from diatoms and other organisms). Importantly, PTMs to silica-binding peptides can be used to control the morphology of precipitated silica, which can allow for the tunable control of silica structures required for various applications. The generation of nano- and microstructures using these silica-binding peptides has various advantages over previously described methodologies.

For example, previous attempts at encapsulating magnetosomes with silicate were performed by the sol-gel method in ~43% ethanol solvent, which is a harsh condition for the magnetosome membrane and proteins (Borg S., et al., Small, 2015 Sep. 2; 11(33): 4209-17). In contrast, the methods described herein facilitate the precipitation of silica in aqueous solvents.

Other applications are limited by time and/or energy constraints. The methods of synthesizing silica described herein are greater than 90% faster than traditional hydrothermal synthesis or sol-gel methods and occur at ambient temperatures (25° C. versus greater than 60° C.) in aqueous conditions (Buckley A. M. and Greenblatt, M. J., J. Chem. Educ., 1994 July; 71(7): 599). Previous examples of combining silica and melanin start with pre-formed silica nanoparticles and require overnight reactions to coat the surfaces with melanin (Schweitzer A. D., et al., Int. J. Radiat. Oncol. Biol. Phys., 2010 Dec. 1; 78(5): 1494-1502). The methodologies described herein, allow one to physically embed melanin molecules in the silica in less than two hours.

Likewise, typical methods to synthesize synthetic opals can take up to a year (usually requiring seven months) and require high temperatures (800-1150° C.) (Filin S. V., et al., Australian Gemmologist, 2002 January; 21: 278-282; U.S. Pat. No. 4,703,020; P.C.T. App. No. PCT/IN2005/000033). The methodologies described herein facilitate the synthesis of opals at room temperature and over the course of days or less.

Synthetic Molecules and Compositions Comprising the Synthetic Molecules

In some aspects the disclosure relates to synthetic molecules. As used herein, the term "synthetic molecule" refers to any non-naturally occurring compound that arises from human engineering. In some embodiments, the synthetic molecule is produced in vitro. In other embodiments, the synthetic molecule is produced in vivo (i.e., in a living organism). In some embodiments, the synthetic molecule is produced in vivo and is subsequently isolated and purified.

In some embodiments, the synthetic molecule comprises an amino acid sequence (i.e., a peptide component). In some embodiments, the amino acid sequence comprises the amino acid sequence of a silica-binding peptide.

The amino acid sequence of various silica-binding peptides are known to those having skill in the art, including the amino acid sequences of R5 (N-SSKKSGSYSGSKGSKR-RIL-C, SEQ ID NO: 1), R1 (N-SSKKSGSYYSYGTKKSG-SYSGYSTKKSASRRIL-C, SEQ ID NO: 2), Si3-3 (N-APPGHHHWHIHH-C, SEQ ID NO: 3), Si3-4 (N-MSASSYASFSWS-C, SEQ ID NO: 4), Si3-8 (N-KP-SHHHHHTGAN-C, SEQ ID NO: 5), Si4-1 (N-MSPHPH-PRHHHT-C, SEQ ID NO: 6), Si4-3 (N-MSPHHMHHSHGH-C, SEQ ID NO: 7), Si4-7 (N-LPHHHHLHTKLP-C, SEQ ID NO: 8), Si4-8 (N-APHHHHPHHLSR-C, SEQ ID NO: 9), Si4-10 (N-RGRRRRLSCRLL-C, SEQ ID NO: 10), and Ge4-1 (N-TVASNSGLRPAS-C, SEQ ID NO: 11) (Kroger N., et al., J. Biol. Chem. 2001 Jul. 13; 276(28): 26066-70; Perry C. C., et al., Biochem. Soc. Trans. 2009 August; 37(Pt 4): 687-91; Baeuerlein E., Wiley-VCH, March 2006; Ch. 1: ISBN: 978-3-527-60461-6). Other previously disclosed R5-like sequences include N-SSKKSGSYSGSKGSKRR(I/N)L-C (SEQ ID NO: 12) and N-SSKKSGSYSGSKG- SKRRNL-C (SEQ ID NO: 13), wherein "N-" and "C-" signify the N-terminus and C-terminus, respectively, of each peptide.

As disclosed herein, the amino acid sequences of additional, non-natural silica-binding peptides include N-GMSSKKSGSKGSKRRIL-C (SEQ ID NO: 14), N-SSEESGSYSGSEGSKRRIL-C (SEQ ID NO: 15), N-SSDDSGSYSGSDGSKRRIL-C (SEQ ID NO: 16), N-SSKESGSYSGSEGSKRRIL-C (SEQ ID NO: 17), N-SSKKSGSYSGSEGSKRRIL-C (SEQ ID NO: 18), N-SSKESGSYSGSKGSKRRIL-C (SEQ ID NO: 19), N-SSKKSGSLSGSKGSKRRIL-C (SEQ ID NO: 20), N-CCKKCGCYCGCKGCKRRIL-C (SEQ ID NO: 21), N-AAKKAGAYAGAKGAKRRIL-C (SEQ ID NO: 22), N-SSKKAGAYAGAKGAKRRIL-C (SEQ ID NO: 23), N-IIKKIGIIIGIKGIKRRIL-C (SEQ ID NO: 24), N-PPKKPGPPPGPKGPKRRIL-C (SEQ ID NO: 25), N-DDKKDGDYDGDKGDKRRIL-C (SEQ ID NO: 26), N-NNEENGNYNGNEGNKRRIL-C (SEQ ID NO: 27), N-NNEKNGNYNGNEGNKRRIL-C (SEQ ID NO: 28), N-HHKKHGHYHGHKGHKRRIL-C (SEQ ID NO: 29), N-KKKKKGKYKGKKGKKRRIL-C (SEQ ID NO: 30), N-EEKKEGEYEGEKGEKRRIL-C (SEQ ID NO: 31), N-AAEEAGAYAGAEGAKRRIL-C (SEQ ID NO: 32), N-AAEKAGAYAGAEGAKRRIL-C (SEQ ID NO: 33), and N-SSHHSGSYSGSHGSKRRIL-C (SEQ ID NO: 34), wherein "N-" and "C-" signify the N-terminus and C-terminus, respectively, of each peptide.

In some embodiments, a synthetic molecule comprises the amino acid sequence of a silica-binding peptide comprising the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, and/or a functional variant, thereof.

In some embodiments, the synthetic molecule comprises an amino acid sequence comprising the amino acid sequence of a silica-binding peptide and at least one terminal fusion molecule, wherein the at least one terminal fusion molecule is fused to at least one terminal end of the amino acid sequence comprising the amino acid sequence of the silica-binding peptide. In the context of a terminal fusion molecule, the term "fused" refers to a covalent attachment formed between the terminal fusion molecule and the N-terminal amine or C-terminal carboxyl group of the amino acid sequence comprising the amino acid sequence of the silica-binding peptide. In some embodiments, a fusion molecule is fused to the N-terminal amine group of the amino acid sequence comprising the amino acid sequence of the silica-binding peptide. In some embodiments, a fusion molecule is fused to the C-terminal carboxyl group of the amino acid sequence comprising the amino acid sequence of the silica-binding peptide. In some embodiments, a fusion molecule is fused to both the N-terminal amine group and the C-terminal carboxyl group of the amino acid sequence comprising the amino acid sequence of the silica-binding peptide. In some embodiments a fusion molecule is fused to the N-terminal amine group of the amino acid sequence comprising the amino acid sequence of the silica-binding peptide, and a separate fusion molecule is fused to the C-terminal carboxyl group of the amino acid sequence comprising the amino acid sequence of the silica-binding peptide.

In some embodiments, at least one of the at least one terminal fusion molecules comprises a biomolecule. As used herein, the term "biomolecule" refers to large molecules generated by an organisms or produced synthetically. In some embodiments, the biomolecule is a macromolecule. Examples of macromolecules include, but are not limited to, proteins (i.e., polypeptides), carbohydrates, lipids, nucleic acids (i.e., polynucleic acids), and combinations thereof. In some embodiments, the biomolecule is a small molecule such as a metabolite, secondary metabolite, or a natural product. Examples of small molecule biomolecules are known to those having ordinary skill in the art.

In some embodiments, at least one of the at least one terminal fusion molecules is a polypeptide that is fused to the at least one terminal end of the amino acid sequence comprising the amino acid sequence of the silica-binding peptide.

In some embodiments, the polypeptide terminal fusion molecule is Mms6 (including Mms6 orthologs and functional variants, thereof). In some embodiments, the polypeptide terminal fusion molecule is MamC (including MamC orthologs and functional variants, thereof). In some embodiments, the polypeptide terminal fusion molecule is a carbon-nanotube-binding peptide. In some embodiments, the carbon-nanotube-binding peptide is CNT1 (including CNT1 orthologs and functional variants, thereof) or CNT2 (including CNT1 orthologs and functional variants, thereof).

In some embodiments, the polypeptide terminal fusion molecule is Cementum Protein 1 (CEMP1) (Chen X., et al., Mater. Sci. Eng. C. Mater. Biol. Appl. 2016 February; 59: 384-89). In some embodiments, the polypeptide terminal molecule is a silicatein protein (see Cha J. N., et al., Proc. Natl. Acad. Sci. U.S.A., 1999 Jan. 19; 96(2): 361-65; Brutchey R. L., et al., J. Am. Chem. Soc. 2006 Aug. 9; 128(31): 10288-94; Sumerel J. L., et al., Chem. Mater. 2003; 15(25): 4804-9, the entirety of which are incorporated herein).

In some embodiments, the polypeptide terminal fusion molecule is a spider silk protein. In some embodiments, the spider silk protein is Major Amullate Spindroin 1 (MaSpl) (SGRGGLGGQGAGMAAAAAMGGAGQGGYGGLG-SQGT, SEQ ID NO: 80) (see Prince J. T., et al., Biochemistry. 1995 Aug. 29; 34: 10879-85, the entirety of which is incorporated herein). In some embodiments, the spider silk protein is fibroin heavy chain (GAGAGSGAAGSG-AGAGSGAGAGSGAGAGSGAGAGSGAGAGSGAGA-GSGAGAGS GAGAGY, SEQ ID NO: 81) or fibroin light chain (see Zafar M. S., et al., Biomacromolecules. 2015; 16(2): 606-14, the entirety of which is incorporated herein).

In some embodiments, the polypeptide terminal fusion molecule is PC Synthase from *S. pompe* (SpPCS) (see Kang S. H., et al., Angew. Chem. Int. Ed. Engl. 2008; 47(28): 5186-89, the entirety of which is incorporated herein).

In some embodiments, the polypeptide terminal fusion molecule is a suckerin protein. In some embodiments, the suckerin protein is Suckerin-39 (see Ding D., et al., Biomacromolecules. 2014; 15: 3278-89, the entirety of which is incorporated herein). In some embodiments the suckerin protein is Suckerin-12 (see Guerette P. A., et al., ACS Nano. 2014 Jul. 22; 8(7): 7170-79, the entirety of which is incorporated herein). In some embodiments, the suckerin protein is the M1 region or M2 region of a suckerin protein. For example, in some embodiments, the suckerin protein is an M1 region amino acid sequence:

| | |
|---|---|
| AATSVSRTTH, | (SEQ ID NO: 82) |
| ATTAVSHTTHHA, | (SEQ ID NO: 83) |
| AATVSHTTHHA, | (SEQ ID NO: 84) |
| AAAVSHTTHHA, | (SEQ ID NO: 85) |
| AAVSHTTHHA, | (SEQ ID NO: 86) |
| AAATVSHTTHHA, or | (SEQ ID NO: 87) |
| AVSHTTHHA. | (SEQ ID NO: 88) |

In some embodiments, the polypeptide terminal fusion molecule is DBAD1 (SEQ ID NO: 35), A1-S1 (SEQ ID NO: 36), A1-S2 (SEQ ID NO: 37), BT1 (SEQ ID NO: 38), BT2 (SEQ ID NO: 39), A7 (SEQ ID NO: 40), Z8 (SEQ ID NO: 41), J182 (SEQ ID NO: 42), J140 (SEQ ID NO: 43), 5R39 (SEQ ID NO: 44), 4R12 (SEQ ID NO: 45), AG-4 (SEQ ID NO: 46), AG-P35 (SEQ ID NO: 47), Col-P10 (SEQ ID NO: 48), CN225 (SEQ ID NO: 49), CN44 (SEQ ID NO: 50), CN179 (SEQ ID NO: 51), CN146 (SEQ ID NO: 52), HG12 (SEQ ID NO: 53), HG6 (SEQ ID NO: 54), Ge8 (SEQ ID NO: 55), Ge34 (SEQ ID NO: 56), Gold-binding peptide a (SEQ ID NO: 57), Gold-binding peptide b (SEQ ID NO: 58), MS-S1 (SEQ ID NO: 59), RE-1 (SEQ ID NO: 60), Ag-22 (SEQ ID NO: 61), Ag-28 (SEQ ID NO: 62), Pt-41 (SEQ ID NO: 63), Pt-14 (SEQ ID NO: 64), Pt-1.2 (SEQ ID NO: 65), HPGAH (SEQ ID NO: 66), AG3 (SEQ ID NO: 67), AG4 (SEQ ID NO: 68), dTi-1(RKK) (SEQ ID NO: 69), Ti-1 (SEQ ID NO: 70), PG-7 (SEQ ID NO: 71), ZnO-la (SEQ ID NO: 72), ZnO-lb (SEQ ID NO: 73), ZnO-2 (SEQ ID NO: 74), ZnO-3 (SEQ ID NO: 75), ZnO-4 (SEQ ID NO: 76), HA 6-1 (SEQ ID NO: 77), HABP1 (SEQ ID NO: 78), or HABP2 (SEQ ID NO: 79) (TABLE 3).

In some embodiments, the polypeptide terminal fusion molecule is a peptide tag. Examples of peptide tags are known to those having skill in the art and include, but are not limited to, AviTag™, Calmodulin-tag, polyglutamate tag, E-tag, FLAG-tag, HA-tag, His-tag, Myc-tag, NE-tag, S-tag, SBP-tag, Softag 1, Softag 3, Strep-tag, TC tag, Ty tag, V5 tag, VSV-tag, Xpress tag, Isopeptag, SpyTag, SnoopTag, BCCP, Glutatione-S-transferase-tag, Green fluorescent protein-tag, Hallo tag, Maltose binding protein-tag, Nus-tag, Thioredoxin-tag, and Fc-tag. In some embodiments, the peptide tag comprise the AviTag™ amino acid sequence (GLNDIFEAQKIEWHE, SEQ ID NO: 89).

In some embodiments, at least one of the at least one terminal fusion molecules is a small molecule that is fused to the at least one terminal end of the amino acid sequence comprising the amino acid sequence of the silica-binding peptide. In some embodiments, the small molecule is biotin. In some embodiments, the small molecule facilitates click reactions; for example, in some embodiments, the small molecule comprises at least one alkyne or aliphatic azide functional group.

In some embodiments, at least one of the at least one terminal fusion molecules does not comprise a biomolecule.

As used herein, the term "functional variant" includes amino acid sequences which are about 70% identical, at least about 80% identical, at least about 90% identical, at least about 95% identical, at least about 98% identical, at least about 99% identical, at least about 99.5% identical, or at least about 99.9% identical to a protein's non-variant amino acid sequence and which retain functionality. The term "functional variant" also includes polypeptides which are shorter or longer than a protein's non-variant amino acid sequence by about 5 amino acids, by about 10 amino acids, by about 15 amino acids, by about 20 amino acids, by about 30 amino acids, by about 40 amino acids, by about 50 amino acids, by about 75 amino acids, by about 100 amino acids or more, and which retain functionality.

In the context of a silica-binding peptide (and functional variants thereof), the term "retain functionality" refers to the variant silica-binding peptide's ability to precipitate silica at least 10%, 20%, 30%, 40%, 50%, 60%, 70%, 80%, 90%, 100%, or more than 100% as efficiently as the non-variant silica-binding peptide. Methods of measuring and comparing levels of silica precipitation are known to those skilled in the art. In the context of Mms6 or MamC (and their orthologs), the term "retain functionality" refers to the protein's ability to bind metal at least 10%, 20%, 30%, 40%, 50%, 60%, 70%, 80%, 90%, 100%, or more than 100% as efficiently as wild-type Mms6 or MamC, respectively. Methods of measuring and comparing levels of magnetosome binding are known to those skilled in the art. In the context of CNT1 or CNT2 (and their orthologs), the term "retain functionality" refers to the protein's ability to bind carbon nanotubes at least 10%, 20%, 30%, 40%, 50%, 60%, 70%, 80%, 90%, 100%, or more than 100% as efficiently as wild-type CNT1 or CNT2, respectively. Methods of measuring and comparing levels of carbon-nanotube-binding are known to those skilled in the art.

In some embodiments, a synthetic molecule consists essentially of the amino acid sequence of a silica-binding peptide comprising the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, and/or a functional variant thereof. As used herein, the term "consists essentially of" refers to situations in which the amino acid sequence is identical to the indicated amino acid sequence, except to the extent that one or more of the amino acids of the amino acid sequence contains a post-translational modification.

In some embodiments, the synthetic molecule comprises the amino acid sequence of a silica-binding peptide and at least one post-translational modification to at least one amino acid of the silica-binding peptide. The term "post-translational modification," as used herein, refers to any covalent modification to the R-group of an amino acid of a synthetic molecule, wherein the covalent modification generates a modified amino acid. As used herein, the term "modified amino acid" refers to any amino acid that is not chemically equivalent or identical to any one of the following amino acids: alanine, arginine, asparagine, aspartic acid, cysteine, glutamine, glutamic acid, glycine, histidine, isoleucine, leucine, lysine, methionine, phenylalanine, proline, serine, tryptophan, tyrosine, and valine. In some embodiments, a post-translational modification is made to the R-group of an amino acid of a synthetic molecule prior to the amino acid's incorporation into the synthetic molecule (i.e., the amino acid molecule is modified prior to peptide-bond formation). In other embodiments, a post-translational modification is made to the R-group of an amino acid of a synthetic molecule after translation or synthesis of a polypeptide component of the synthetic molecule (i.e., the R group of an amino acid of a synthetic molecule is modified after it is incorporated into the synthetic molecule).

Various post-translational modifications are known to those having skill in the art, including, but not limited to, acylation (e.g., O-acylation, N-acylation, S-acylation), acetylation, adenylylation, alkylation (e.g., methylation), amidation, arginylation, biotinylation, butyrylation, carbamylation, carbonylation, carboxylation (e.g., gamma-carboxylation), farnesylation, formylation, geranylgeranylation, glycation, glycosylation (e.g., polysialyation), glutathionylation, glypiation, hypusination, hydryoxylation, iodination, isoprenylation, lipoylation, malonylation, myristoylation, nirtosylation, oxidation, palmitoylation, pegylation, phosphopantetheinylation, phosphorylation, polyglutamylation, polyglycylation, propionylation, propylamination (e.g., the addition of spermine, spermidine, thermospermine, putrescine, and other long chain polyamines), pyroglutamination, ribosylation, succinylation, sulfation, sulfenylation, sulfinylation, sulfonation, and sulfonylation.

In some embodiments, at least one of the at least one non-native post-translational modifications is selected from the group consisting of acylation (e.g., O-acylation, N-acylation, S-acylation), acetylation, adenylylation, alkylation (e.g., methylation), amidation, arginylation, biotinylation, butyrylation, carbamylation, carbonylation, carboxylation (e.g., gamma-carboxylation), farnesylation, formylation, geranylgeranylation, glycation, glycosylation (e.g., polysialyation), glutathionylation, glypiation, hypusination, hydryoxylation, iodination, isoprenylation, lipoylation, malonylation, myristoylation, nirtosylation, oxidation, palmitoylation, pegylation, phosphopantetheinylation, phosphorylation, polyglutamylation, polyglycylation, propionylation, propylamination, pyroglutamination, ribosylation, succinylation, sulfation, sulfenylation, sulfinylation, sulfonation, and sulfonylation.

In some embodiments, the synthetic molecule comprises a single post-translational modification. In other embodiments, the synthetic molecule comprises more than one post-translational modification. In other embodiments, the synthetic molecule comprises more than one post-translational modification, wherein none of the post-translational modifications are equivalent (i.e., no amino acid has the same post-translation modification). In other embodiments, at least two of the amino acids of the synthetic molecule have the same post-translational modification. In some embodiments, at least two of the amino acids of the synthetic molecule have a different post-translational modification.

In some embodiments, the synthetic molecule comprises the amino acid sequence of a silica-binding peptide and at least one non-native post-translational modification to at least one amino acid of the silica-binding peptide. The term "non-native post-translational modification," as used herein, refers to a post-translational modification to a synthetic molecule (or a combination of post-translational modifications to a synthetic molecule), wherein the post-translational modification of the synthetic molecule (or the combination of post-translational modifications to the synthetic molecule) does not occur in nature. For example, in some embodiments, the synthetic molecule comprises an amino acid sequence that is not found in nature. In these instances, the term "non-native post-translational modification" encompasses any post-translational modification to the synthetic molecule.

In other embodiments, the synthetic molecule consists essentially of the amino acid sequence of a peptide that occurs in nature (i.e., a naturally occurring amino acid sequence). For example, in some embodiments, the synthetic molecule consists essentially of the amino acid sequence of R5 (SEQ ID NO: 1), wherein the amino acid sequence comprises at least one non-native post-translational modification of the amino acid sequence of R5. R5 represents the amino acid sequence of silaffin-$1A_1$ which is encoded by the sill gene of the diatom *C. fusiformis*. The amino acid sequence of silaffin-$1A_1$ is post-translationally modified, in at least some contexts, by *C. fusiformis* in nature. For example, previous studies have demonstrated that the R5 amino acid sequence is modified in nature by phosphorylation (occurring at each serine residue), methylation (on Lys4 and Lys12), and propylamination (on Lys3 and Lys15). However, some post-translational modifications to the R5 amino acid sequence (or combinations of post-translational modifications to the R5 amino acid sequence) do not occur in nature (i.e., are non-native post-translational modifications). For example, methylation can be introduced on one or more Lys residues of the R5 amino acid sequence that are not methylated by *C. fusiformis*. Moreover, the Lys residues of the R5 amino acid sequence that are methylated by *C. fusiformis* can be methylated to a non-native extent (e.g., through the introduction of mono-, di- or tri-methylation).

In summary, in the context of a synthetic molecule consisting essentially of a naturally-occurring amino acid sequence and at least one non-native post-translational modification to the naturally-occurring amino acid sequence, the term "non-native post-translational modification" encompasses any covalent modification to the R-group of any amino acid of the naturally-occurring amino acid sequence (or any combination of covalent modifications to the R-group of more than one amino acid of the naturally-occurring amino acid sequence) that does not occur in any organism that produces the naturally-occurring amino acid sequence in nature.

In some aspects, the disclosure relates to compositions comprising at least one synthetic molecule as described above. As used herein, the term "composition" refers to any mixture of compounds, wherein the compounds are not covalently connected. In addition to the at least one synthetic molecules described herein, a composition may also comprise salts, solvents, buffers, stabilizing agents, and/or protease inhibitors. The compositions can take the form of solutions, suspensions, emulsion, powders, solids and the like. In some embodiments, the composition comprises two or more types of synthetic molecules, wherein the two or more types of synthetic molecules are chemically unique.

Polymers and Compositions Comprising the Polymers

In some aspects, the disclosure relates to a polymer comprising a fusion of at least two synthetic molecules, wherein the synthetic molecules are as described above in "Synthetic Molecules and Compositions Comprising the Synthetic Molecules." In the context of a polymer comprising the fusion of at least two synthetic molecules, the terms "fusion" and "fused" refer to a covalent bond formed between: 1) at least one amino acid side chain of at least two of the at least two synthetic molecules of the polymer; 2) at least one terminal end of each of at least two of the at least two synthetic molecules; and/or 3) at least one terminal end of at least one of the at least two synthetic molecules and at least one amino acid side chain of at least one of the at least two synthetic molecules.

In some embodiments, a polymer comprises at least two, three, four, five, six, seven, or eight synthetic molecules that are fused through an interaction between at least one amino acid side chain of each of the at least two, three, four, five, six, seven, or eight synthetic molecules of the polymer. In some embodiments, a polymer comprises at least two synthetic molecules that are fused through an interaction between at least one amino acid side chain of each of the at least two synthetic molecules.

In some embodiments, a polymer comprises at least two, three, four, five, six, seven, or eight synthetic molecules that are fused through an interaction between at least one terminal end of each of the at least two, three, four, five, six, seven, or eight synthetic molecules. In some embodiments, a polymer comprises at least two synthetic molecules that are fused through an interaction between at least one terminal end of each of the at least two synthetic molecules.

In some embodiments, a polymer comprises at least two, three, four, five, six, seven, or eight synthetic molecules that are fused through at least one terminal end of at least one of the at least two, three, four, five, six, seven, or eight synthetic molecule and at least one amino acid side chain of at least one of the at least two, three, four, five, six, seven, or eight synthetic molecules. In some embodiments, a polymer comprises at least two synthetic molecules that are fused through at least one terminal end of at least one of the at least two synthetic molecule and at least one amino acid side chain of at least one of the at least two synthetic molecules.

In some embodiments, a polymer is a linear polymer. In some embodiments, a polymer is an alternating polymer (e.g., A-B-A-B-A-B). In some embodiments, a polymer is a periodic polymer (e.g., (A-B-A-A-B)). In some embodiments, the polymer is a statistical polymer. In some embodiments, the polymer is a block polymer (e.g., a diblock or triblock polymer). In some embodiments, a polymer is a branched polymer. In some embodiments, the polymer is a star, brush, or comb polymer.

In some embodiments, a polymer comprises at least two synthetic molecules that are fused through a single covalent bond. In other embodiments, a polymer comprises comprising at least two synthetic molecules that are fused through at least two covalent bonds.

In some embodiments, a polymer comprises a fusion of at least two synthetic molecules, and each of the at least two synthetic molecules are identical. In other embodiments, at least two of the at least two synthetic molecules are chemically unique (i.e., are not made up of the same atoms).

In some embodiments, a polymer comprises a fusion of at least two synthetic molecules, wherein at least two of the synthetic molecules comprise the amino acid sequence of a silica-binding peptide. In some embodiments, the polymer comprises R5-melanin.

In some embodiments, a polymer comprises a fusion of at least two synthetic molecules, wherein at least two of the synthetic molecules comprise the amino acid sequence of a silica-binding peptide and wherein at least one of the silica binding peptides comprises the amino acid sequence of R5 and the amino acid sequence of an M1 or M2 region of a suckerin protein, e.g., to make di-block or tri-block copolymers.

In some aspects, the disclosure relates to a composition comprising at least one polymer as described above. As used herein, the term "composition" refers to any mixture of compounds, wherein the compounds are not covalently connected. In addition to the at least one synthetic molecules described herein, a composition may also comprise salts, solvents, buffers, stabilizing agents, and/or protease inhibitors. The compositions can take the form of solutions, suspensions, emulsion, powders, solids and the like. In some embodiments, the composition comprises two or more types of polymers, wherein the two or more types of polymers are chemically unique.

Methods of Generating Synthetic Molecules and Polymers

In some aspects, the disclosure relates to the methods of generating synthetic molecules as described above in "Synthetic Molecules and Compositions Comprising the Synthetic Molecules." In some embodiments, the method comprises sequentially contacting an amino acid with another amino acid under conditions that facilitate the generation of peptide bonds between the amino acids (i.e., the generation of a peptide). In some embodiments, at least one of the amino acids is a modified amino acid. Methods of generating peptides in vitro and in vivo are known to those having skill in the art.

In some embodiments, the generated peptide is a silica-binding peptide.

In some embodiments, the method further comprises contacting the silica-binding peptide with a modifying enzyme, wherein the modifying enzyme introduces post-translational modifications to the R-group of at least one amino acid of the silica-binding peptide.

In some embodiments the modifying enzyme is capable of phosphorylating the R-group of at least one amino acid of the silica-binding peptide. Examples of known and putative modifying enzymes that are capable of phosphorylating an amino acid R-group of a peptide have been identified by those having skill in the art and include, but are not limited to, BRSK2, THAPSDRAFT_34059, THAPS_35643, THAPSDRAFT_33728, Ca2+/calmodulin dependent protein kinase II, DAP Kinase, GSK3a, GSK33, PKA (protein kinase A), and LKB1 (liver kinase B1).

In some embodiments the modifying enzyme is capable of methylating the R-group of at least one amino acid of the silica-binding peptide. Examples of known and putative modifying enzymes that are capable of methylating an amino acid R-group of a peptide have been identified by those having skill in the art and include, but are not limited to, SET7/9 gi_71042599, gi_512853798, gi_16754879, THAPSDRAFT_20746, THAPSDRAFT_32876, THAPSDRAFT_21274, THAPSDRAFT_11244, THAPSDRAFT_24355, THAPSDRAFT_30620, THAPSDRAFT_263816, THAPS_41291, THAPSDRAFT_23288, cffcpA-2, SIT4A, SIT2, DSK1, MAP2, RPC25, THAPSDRAFT_35182, THAPSDRAFT_268872, THAPSDRAFT_22056, THAPSDRAFT_3607, THAPSDRAFT_bd1835, THAPSDRAFT_11154, THAPSDRAFT_11069, THAPSDRAFT_268872, THAPSDRAFT_23212, THAPSDRAFT_5135, THAPSDRAFT_23725, MET, rbcMT, PHATRDRAFT_55013, PHATRDRAFT_51541, PHATRDRAFT_46484, PHATRDRAFT_47888, PHATDRAFT_45376, PHATRDRAFT_6698, PHATRDRAFT_42601, LCYB. THAPSDRAFT_21409, THAPSDRAFT_8998, THAOC_37500, and THAOC_24272.

In some embodiments the modifying enzyme is capable of propylaminating the R-group of at least one amino acid of the silica-binding peptide. Examples of known and putative modifying enzymes that are capable of propylaminating an amino acid R-group of a peptide have been identified by those having skill in the art and include, but are not limited to, ACL5, THAPSDRAFT_17140, THAPSDRAFT_23207, THAPSDRAFT_24273, THAPSDRAFT_24769, THAPSDRAFT_261161, THAPSDRAFT_262580, THAPSDRAFT_264237, THAPSDRAFT_264730, THAPSDRAFT_267946, TPS_41289, TPS_108361, SPDS, SPMS, tSPMS, PMT, SpeD, THAPSDRAFT_21371, THAPS-DRAFT_269901, and THAPSDRAFT_30691.

In some embodiments the modifying enzyme is capable of hypusinating the R-group of at least one amino acid of the silica-binding peptide. Examples of known and putative modifying enzymes that are capable of hypusinating an amino acid R-group of a peptide have been identified by those having skill in the art and include, but are not limited to, DHPS and DOHH.

In some embodiments the modifying enzyme is capable of hydroxylating the R-group of at least one amino acid of the silica-binding peptide. Examples of known and putative modifying enzymes that are capable of hydroxylating an amino acid R-group of a peptide have been identified by those having skill in the art and include, but are not limited to, JMJD6, JMJD6, THAOC_04424, THAOC_27572, PHATRDRAFT_3251, PHATRDRAFT_49314, THAPS-DRAFT_8036, THAPSDRAFT_7775, Lysyl Hydroxylase 3 (LH3), Lysyl Hydroxylase 2 (LH2), Lysyl Hydroxylase 1 (LH1), and Procollagen-lysine, 2-oxoglutarate 5-dioxygenase 1 (PLOD1).

In some embodiments the modifying enzyme is capable of adenylylating the R-group of at least one amino acid of the silica-binding peptide. Examples of known and putative modifying enzymes that are capable of adenylylating an amino acid R-group of a peptide have been identified by those having skill in the art and include, but are not limited to, vopS.

In some embodiments the modifying enzyme is capable of biotinylating the R-group of at least one amino acid of the silica-binding peptide. Examples of known and putative modifying enzymes that are capable of biotinylating an amino acid R-group of a peptide have been identified by those having skill in the art and include, but are not limited to, BirA.

In some embodiments the modifying enzyme is capable of glycosylating the R-group of at least one amino acid of the silica-binding peptide. Examples of known and putative modifying enzymes that are capable of glycosylating an amino acid R-group of a peptide have been identified by those having skill in the art and include, but are not limited to, GALNT1, OGT, POMT1, THAPSDRAFT_3500, POFUT1 (GDP-frucose protein O-fucosyltransferase 1), POFUT2 (GDP-frucose protein O-fucosyltransferase 2), and POMT1 (Protein O-mannosyl-transferase 1).

In some embodiments the modifying enzyme is capable of lapidating the R-group of at least one amino acid of the silica-binding peptide. Examples of known and putative modifying enzymes that are capable of lapidating an amino acid R-group of a peptide have been identified by those having skill in the art and include, but are not limited to, LpA, LipB, LIPT1, NMT2, and NMT1.

In some embodiments the modifying enzyme is capable of acetylating the R-group of at least one amino acid of the silica-binding peptide. Examples of known and putative modifying enzymes that are capable of acetylating an amino acid R-group of a peptide have been identified by those having skill in the art and include, but are not limited to, LAT2, THAPSDRAFT_2540, ELP3, HAT1, GCN5, KAT2A, p300 (ElA-associated protein 300 kDa), MOZ, YBF2/Sas3, Sas2, Tip60, Morf, and Crebbp.

In some embodiments the modifying enzyme is capable of sulfonating the R-group of at least one amino acid of the silica-binding peptide. Examples of known and putative modifying enzymes that are capable of sulfonating an amino acid R-group of a peptide have been identified by those having skill in the art and include, but are not limited to, TPST1 (Protein-tyrosine sulfotransferase 1) and TPST2 (Protein-tyrosine sulfotransferase 2).

In some embodiments, the method further comprises contacting the silica-binding peptide with a terminal fusion molecule under such conditions that facilitate the generation of at least one covalent bond between the N-terminal amino and/or C-terminal carboxyl group of the silica-binding peptide and the terminal fusion protein.

In some embodiments, at least one of the at least one terminal fusion molecules comprises a biomolecule. In some embodiments, at least one of the at least one terminal fusion molecules is a polypeptide that is fused to at least one terminal end of the amino acid sequence comprising the amino acid sequence of the silica-binding peptide. In some embodiments, the polypeptide that is fused to the at least terminal end of the silica-binding peptide as the polypeptide is synthesized. For example, in some embodiments, the silica-binding peptide is synthesized and then the terminal fusion polypeptide is synthesized on the C-terminal end of the amino acid sequence comprising the amino acid sequence of the silica-binding protein. In other embodiments, the terminal fusion polypeptide is synthesized and then the silica-binding peptide is synthesized on the C-terminal end of the terminal fusion polypeptide.

In some embodiments, the polypeptide terminal fusion molecule comprises the amino acid sequence of Mms6 (including Mms6 orthologs and functional variants, thereof). In some embodiments, the polypeptide terminal fusion molecule comprises the amino acid sequence of MamC (including MamC orthologs and functional variants, thereof). In some embodiments, the polypeptide terminal fusion molecule comprises the sequence of a carbon-nanotube-binding peptide. In some embodiments, the carbon-nanotube-binding peptide is CNT1 (including CNT1 orthologs and functional variants, thereof) or CNT2 (including CNT1 orthologs and functional variants thereof).

In some embodiments, the polypeptide terminal fusion molecule is Cementum Protein 1 (CEMP1) (Chen X., et al., Mater. Sci. Eng. C. Mater. Biol. Appl. 2016 February; 59: 384-89). In some embodiments, the polypeptide terminal molecule is a silicatein protein (see Cha J. N., et al., Proc. Natl. Acad. Sci. U.S.A., 1999 Jan. 19; 96(2): 361-65; Brutchey R. L., et al., J. Am. Chem. Soc. 2006 Aug. 9; 128(31): 10288-94; Sumerel J. L., et al., Chem. Mater. 2003; 15(25): 4804-9, the entirety of which is incorporated herein).

In some embodiments, the polypeptide terminal fusion molecule is a spider silk protein. In some embodiments, the spider silk protein is Major Amullate Spindroin 1 (MaSpl) (SGRGGLGGQGAGMAAAAAMGGAGQGGYGGLGS-QGT, SEQ ID NO: 80) (see Prince J. T., et al., Biochemistry. 1995 Aug. 29; 34: 10879-85, the entirety of which is incorporated herein). In some embodiments, the spider silk protein is fibroin heavy chain (GAGAGSGAAGSGA-GAGSGAGAGSGAGAGSGAGAGSGAGAGSGAGAG-SGAGAGS GAGAGY, SEQ ID NO: 81) or fibroin light chain (see Zafar M. S., et al., Biomacromolecules. 2015; 16(2): 606-14, the entirety of which is incorporated herein).

In some embodiments, the polypeptide terminal fusion molecule is PC Synthase from *S. pompe* (SpPCS) (see Kang S. H., et al., Angew. Chem. Int. Ed. Engl. 2008; 47(28): 5186-89, the entirety of which is incorporated herein).

In some embodiments, the polypeptide terminal fusion molecule is a suckerin protein. In some embodiments, the suckerin protein is Suckerin-39 (see Ding D., et al., Biomacromolecules. 2014; 15: 3278-89, the entirety of which is incorporated herein). In some embodiments the suckerin protein is Suckerin-12 (see Guerette P. A., et al., ACS Nano.

2014 Jul. 22; 8(7): 7170-79, the entirety of which is incorporated herein). In some embodiments, the suckerin protein is the M1 region or M2 region of a suckerin protein. For example, in some embodiments, the suckerin protein is an M1 region amino acid sequence:

| | |
|---|---|
| AATSVSRTTH, | (SEQ ID NO: 82) |
| ATTAVSHTTHHA, | (SEQ ID NO: 83) |
| AATVSHTTHHA, | (SEQ ID NO: 84) |
| AAAVSHTTHHA, | (SEQ ID NO: 85) |
| AAVSHTTHHA, | (SEQ ID NO: 86) |
| AAATVSHTTHHA, or | (SEQ ID NO: 87) |
| AVSHTTHHA. | (SEQ ID NO: 88) |

In some embodiments, the polypeptide terminal fusion molecule is DBAD1 (SEQ ID NO: 35), A1-S1 (SEQ ID NO: 36), A1-S2 (SEQ ID NO: 37), BT1 (SEQ ID NO: 38), BT2 (SEQ ID NO: 39), A7 (SEQ ID NO: 40), Z8 (SEQ ID NO: 41), J182 (SEQ ID NO: 42), J140 (SEQ ID NO: 43),5R39 (SEQ ID NO: 44),4R12 (SEQ ID NO: 45), AG-4 (SEQ ID NO: 46), AG-P35 (SEQ ID NO: 47), Col-P10 (SEQ ID NO: 48), CN225 (SEQ ID NO: 49), CN44 (SEQ ID NO: 50), CN179 (SEQ ID NO: 51), CN146 (SEQ ID NO: 52), HG12 (SEQ ID NO: 53), HG6 (SEQ ID NO: 54), Ge8 (SEQ ID NO: 55), Ge34 (SEQ ID NO: 56), Gold-binding peptide a (SEQ ID NO: 57), Gold-binding peptide b (SEQ ID NO: 58), MS-S1 (SEQ ID NO: 59), RE-1 (SEQ ID NO: 60), Ag-22 (SEQ ID NO: 61), Ag-28 (SEQ ID NO: 62), Pt-41 (SEQ ID NO: 63), Pt-14 (SEQ ID NO: 64), Pt-1.2 (SEQ ID NO: 65), HPGAH (SEQ ID NO: 66), AG3 (SEQ ID NO: 67), AG4 (SEQ ID NO: 68), dTi-1(RKK) (SEQ ID NO: 69), Ti-1 (SEQ ID NO: 70), PG-7 (SEQ ID NO: 71), ZnO-la (SEQ ID NO: 72), ZnO-lb (SEQ ID NO: 73), ZnO-2 (SEQ ID NO: 74), ZnO-3 (SEQ ID NO: 75), ZnO-4 (SEQ ID NO: 76), HA 6-1 (SEQ ID NO: 77), HABP1 (SEQ ID NO: 78), or HABP2 (SEQ ID NO: 79) (TABLE 3).

In some embodiments, the polypeptide terminal fusion molecule is a peptide tag. Examples of peptide tags are known to those having skill in the art and include, but are not limited to, AviTag™, Calmodulin-tag, polyglutamate tag, E-tag, FLAG-tag, HA-tag, His-tag, Myc-tag, NE-tag, S-tag, SBP-tag, Softag 1, Softag 3, Strep-tag, TC tag, Ty tag, V5 tag, VSV-tag, Xpress tag, Isopeptag, SpyTag, SnoopTag, BCCP, Glutatione-S-transferase-tag, Green fluorescent protein-tag, Hallo tag, Maltose binding protein-tag, Nus-tag, Thioredoxin-tag, and Fc-tag. In some embodiments, the peptide tag comprise the AviTag™ amino acid sequence (GLNDIFEAQKIEWHE, SEQ ID NO: 89)

In some embodiments, at least one of the at least one terminal fusion molecules is a small molecule that is fused to the at least one terminal end of the amino acid sequence comprising the amino acid sequence of the silica-binding peptide. In some embodiments, the small molecule is biotin. In some embodiments, the small molecule facilitates click reactions; for example, in some embodiments, the small molecule comprises at least one alkyne or aliphatic azide functional group.

In some embodiments, at least one of the at least one terminal fusion molecules is not a biomolecule.

In some aspects, the disclosure relates to methods of generating polymers as described above in "Polymers and Compositions Comprising the Polymers." In some embodiments, the method comprises, contacting at least two synthetic molecules under conditions that facilitate the generation of at least one covalent bond between the at least two synthetic molecules. In some embodiments, at least one of the at least one covalent bonds is formed between at least one amino acid side chain of each of the synthetic molecules of the polymer. In some embodiments, at least one of the at least one covalent bonds is formed between at least one terminal end of each synthetic molecule. In some embodiments, at least one of the at least one covalent bonds is formed between at least one terminal end of at least one synthetic molecule and at least one amino acid side chain of another synthetic molecule.

Silica Structures

In some aspects, the disclosure relates to a silica structures comprising precipitated silica and at least one synthetic molecule, wherein the at least one synthetic molecule is as described above in "Synthetic Molecules and Compositions Comprising the Synthetic Molecules." In some embodiments, the silica structure further comprises at least one metal nanoparticle. In some embodiments, at least one of the at least one metal nanoparticles is selected from the group consisting of an iron oxide nanoparticle, a zinc oxide nanoparticle, tantalum oxide nanoparticles, a hafnium oxide nanoparticle, a titanium oxide nanoparticle, a cadmium sulfide nanoparticle, a germanium oxide nanoparticle, an indium phosphide, and a cadmium selenide nanoparticle. In some embodiments, the silica structure further comprises at least one magnetosome. In some embodiments, the silica structure further comprises a biomolecule. In some embodiments, the biomolecule is DNA.

In some embodiments, at least one of the at least one synthetic molecules is R5-Mms6 as described in Example 10. In some embodiments, at least one of the at least one synthetic molecules is R5-MamC as described in Example 11. In some embodiments, at least one of the at least one synthetic molecules is R5-CNT. In some embodiments, the R5-CNT is R5-CNT1 as described in Example 12. In some embodiments, the R5-CNT is R5-CNT2 as described in Example 12.

In some aspects, the disclosure relates to a silica structure comprising precipitated silica and at least one polymer, wherein the at least one polymer is as described above in "Polymers and Compositions Comprising the Polymers." In some embodiments, at least one of the at least one polymers comprises R5-melanin as described in Example 9.

In some aspects, the disclosure relates to a silica coated DNA-nanostructure comprising precipitated silica, R5 peptide, and DNA; for example, as described in Example 13.

Methods of Synthesizing Silica Structures and Resulting Silica Structures

In some aspects, the disclosure relates to methods of synthesizing silica structures. In some embodiments, the method comprises: contacting at least one synthetic molecule (as described above in "Synthetic Molecules and Compositions Comprising the Synthetic Molecules") with a solution comprising dissolved silica. In some embodiments, the at least one synthetic molecule and the solution comprising dissolved silica are contacted at ambient temperature (as used herein, the term "ambient temperature" refers to temperatures range of about 18° C. to about 30° C. In some embodiments, the at least one synthetic molecule and the solution comprising dissolved silica are contacted at chilled temperatures. As used herein, the term "chilled temperatures" refers to temperatures range of about 0° C. to about 4° C.

In some embodiments, the dissolved silica is aqueous silicic acid. In some embodiments, the dissolved silica is colloidal silica.

In some embodiments, the method further comprises contacting the at least one synthetic molecule and the solution comprising dissolved silica with at least one metal nanoparticle. In some embodiments, at least one of the at least one metal nanoparticles is selected from the group consisting of an iron oxide nanoparticle, a zinc oxide nanoparticle, tantalum oxide nanoparticles, a hafnium oxide nanoparticle, a titanium oxide nanoparticle, a cadmium sulfide nanoparticle, a germanium oxide nanoparticle, an indium phosphide, and a cadmium selenide nanoparticle.

In some embodiments, the method further comprises contacting the synthetic molecule and the solution comprising dissolved silica with magnetosomes.

In some embodiments, the method further comprises contacting the synthetic molecule and the solution comprising dissolved silica with a biomolecule. In some embodiments, the biomolecule is DNA.

In some aspects, the disclosure relates to a melanin embedded silica structure generated by a method as described above; see for example, Example 9.

In some aspects, the disclosure relates to an R5-Mms6 iron oxide nanoparticle silica structure as generated by a method as described above; see for example, Example 10.

In some aspects, the disclosure relates to an R5-MamC magnetosome silica structure generated by a method as described above; see for example, Example 11.

In some aspects, the disclosure relates to a carbon-nanotube-binding magnetosome silica structure generated by a method as described above; see for example, Example 12.

In some aspects, the disclosure relates to an opal silica structure generated by the method a method as described above; see for example, Example 14.

In some aspects, the disclosure relates to methods of synthesizing silica-coated DNA-nanostructures; see for example, Example 13. In some embodiments, the method comprises contacting DNA with R5 peptide and subsequently contacting the DNA and R5 peptide with a solution comprising dissolved silica. In some embodiments, the DNA and the R5 are contacted with the solution comprising dissolved silica at ambient temperature. In some embodiments, the dissolved silica is aqueous silicic acid. In some embodiments, the dissolved silica is colloidal silica.

EXAMPLES

Example 1: Post-Translational Modification of the R5 Peptide

The R5 peptide (N-SSKKSGSYSGSKGSKRRIL-C) (SEQ ID NO: 1) from the diatom *Cylindrotheca fusiformis* was previously shown to precipitate 500 nm diameter silica spheres in vitro (Kröger N., et al., Science, 1999 Nov. 5; 286(5442): 1129-32). For the experiments described below, R5 was recombinantly expressed in *Escherichia coli* (*E. coli*) and R5 peptide was purified by affinity and size exclusion chromatography. The purified peptide was lyophilized and then resuspended to a concentration of 5 mM in water.

As demonstrated herein, the R5 peptide can be modified with non-native post-translational modifications (PTMs) in vitro using modifying enzymes isolated from various organisms (both from diatoms and other organisms) or recombinantly expressed in *E. coli*. The data described below using polymerized R5 peptides indicates that PTMs to R5 can be used to control the morphology of precipitated silica, which will allow for the tunable control of silica structures required for various applications.

Example 2: Generation of Phosphorylated R5 Peptide

Protein Kinase A (PKA) (NEB P6000S) was incubated with kinase buffer (NEB B6022S), 2 µM R5, and 1 mM ATP at 30° C. for 30 minutes to 16 hours, followed by heat inactivation at 65° C. for 20 minutes. A time course showing the incorporation of one phosphate into R5 was determined by LC-MS (FIG. 1A). Varying the ratio of PKA to R5 (up to 1000U:2 µM was tested) could increase the proportion of phosphorylated R5 to 66% of the total R5 population (FIG. 1B). LC-MS/MS was performed using an Agilent QQQ and indicated primary phosphorylation at Ser11, with very low levels of phosphorylation at Ser4, Ser7, and Ser16 (FIG. 1C).

Example 3: Generation of Methylated R5 Peptide

Figure 2B:
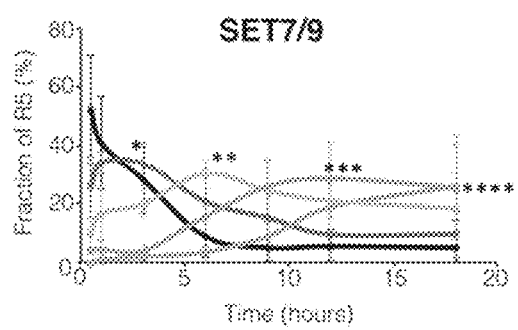

SET7/9 was recombinantly expressed in *E. coli* (Addgene, plasmid #24082) and purified by affinity chromatography. Purified lysine methyltransferase SETD7 (SET7/9) was incubated with methylation buffer (50 mM Tris-HCl, pH 9.0, 5 mM MgCl$_2$, 4 mM DTT), 2 µM R5, and 16 µM SAM at 37° C. for 30 minutes to 18 hours, followed by heat inactivation at 65° C. for 20 minutes. A time course showing the incorporation of zero to 16 methyl groups into R5 (FIG. 2A) and profile traces for zero through four methyl groups (FIG. 2B) were determined by LC-MS.

Figure 2C:
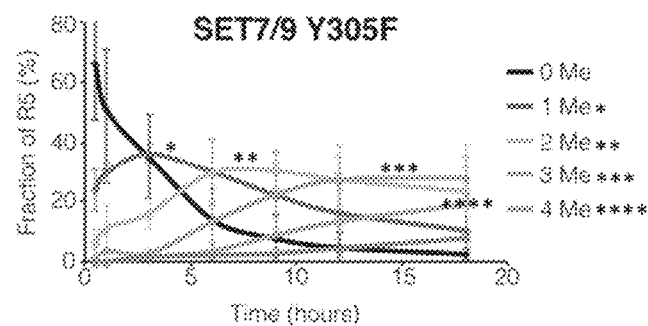

The Y305F mutation was introduced into SET7/9 (Addgene, plasmid #24082) by site-directed mutagenesis. SET7/9 Y305F was recombinantly expressed in *E. coli* and purified by affinity chromatography. Purified SET7/9 Y305F was incubated with methylation buffer (50 mM Tris-HCl, pH 9.0, 5 mM MgCl$_2$, 4 mM DTT), 2 µM R5, and 16 µM SAM at 37° C. for 30 minutes to 18 hours, followed by heat inactivation at 65° C. for 20 minutes. A time course showing the incorporation of zero to 16 methyl groups into R5 (FIG. 2A) and profile traces for zero through four methyl groups (FIG. 2C) were determined by LC-MS.

Figure 3A:
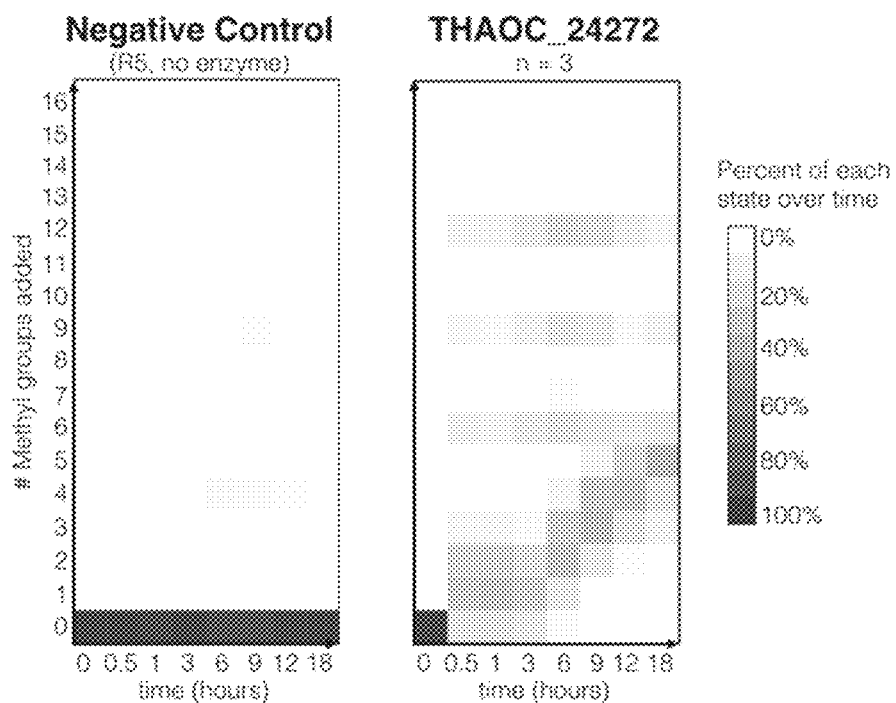
FIGS. 3A-3C. Methylation of R5 by diatom protein THAOC_24272.
Figure 3B:
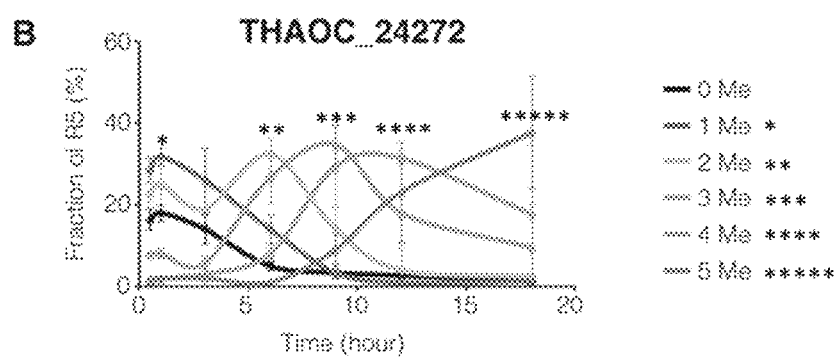
Figure 3C:
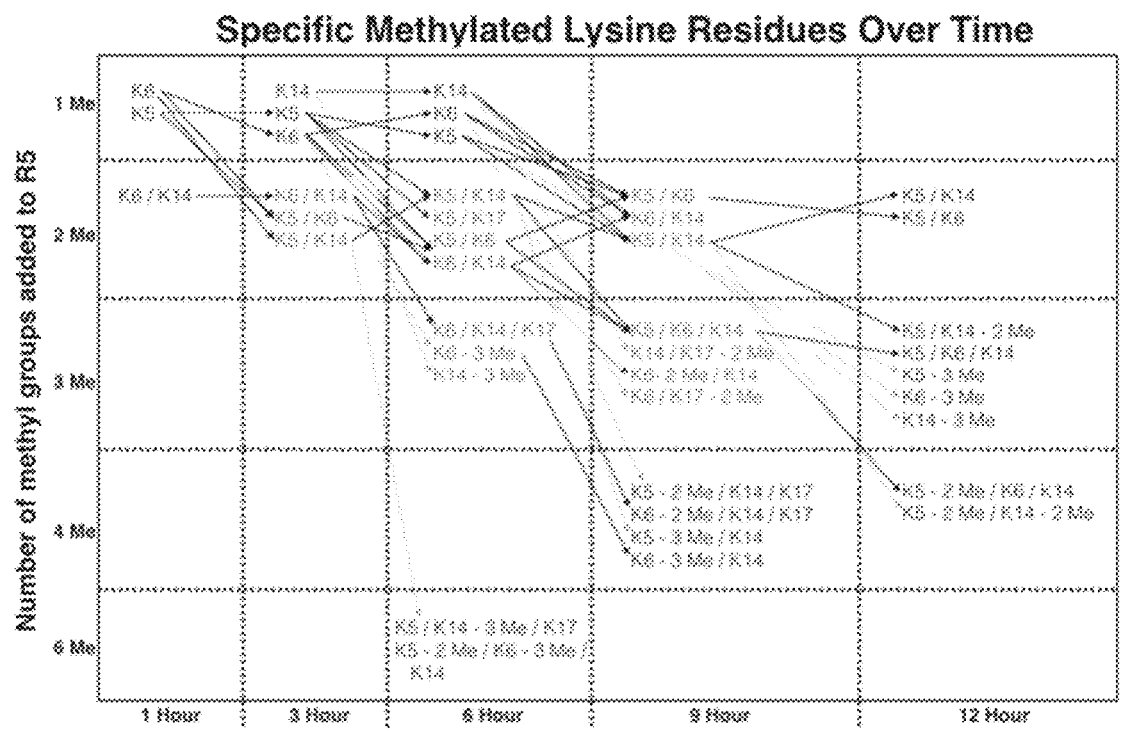

THAOC_24272 is a previously uncharacterized hypothetical protein from the diatom *Thalassiosira oceanica* (THAOC_24272—uniprot.org/uniprot/KORQ67). The gene was identified as containing a Rubisco large subunit methyltransferase (LSMT) binding site via BLAST. The gene was optimized for expression in *E. coli*, synthesized, transformed into *E. coli*, expressed, and purified by affinity chromatography. Purified THAOC_24272 was incubated with methylation buffer (50 mM Tris-HCl, pH 9.0, 5 mM MgCl$_2$, 4 mM DTT), 2 µM R5, and 16 µM SAM at 37° C. for 30 minutes to 18 hours, followed by heat inactivation at 65° C. for 20 minutes. A time course showing the incorporation of zero to 16 methyl groups into R5 (FIG. 3A) and profile traces for zero through five methyl groups (FIG. 3B) were determined by LC-MS. LC-MS/MS were performed using Agilent QQQ and Thermo Orbitrap instruments and indicated the methylation occurs on all four lysine with no discernable preference or pattern (FIG. 3C).

Figure 4A:
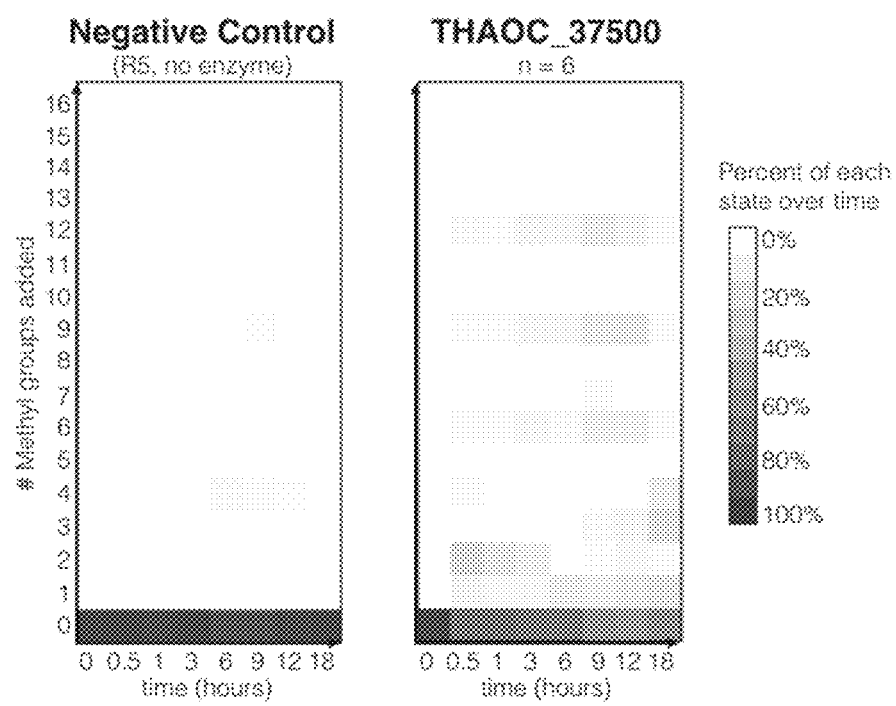
FIGS. 4A-4B. Methylation of R5 by diatom protein THAOC_37500.
Figure 4B:
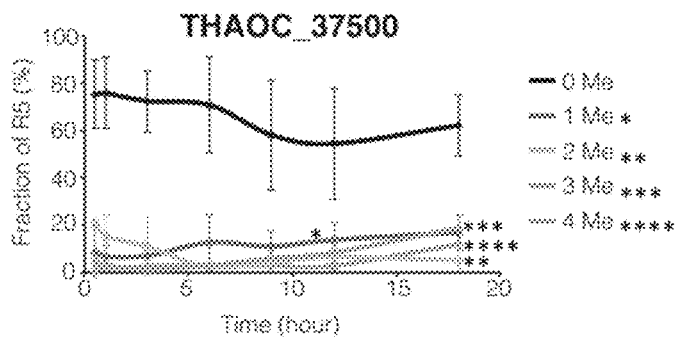

THAOC_37500 is a previously uncharacterized hypothetical protein from the diatom *Thalassiosira oceanica* (THAOC_37500—uniprot.org/uniprot/KOQYB9). The gene was identified as containing a Rubisco large subunit methyltransferase (LSMT) binding site via BLAST. The gene was optimized for expression in *E. coli*, synthesized, transformed into *E. coli*, expressed, and purified by affinity chromatography. Purified THAOC_37500 was incubated with methylation buffer (50 mM Tris-HCl, pH 9.0, 5 mM MgCl$_2$, 4 mM DTT), 2 µM R5, and 16 µM SAM at 37° C. for 30 minutes to 18 hours, followed by heat inactivation at 65° C. for 20 minutes. A time course showing the incorporation of zero to 16 methyl groups into R5 (FIG. 4A) and profile traces for zero through four methyl groups (FIG. 4B) were determined by LC-MS.

Example 4: Generation of Thermospermine-Modified R5 Peptide

Figure 5:
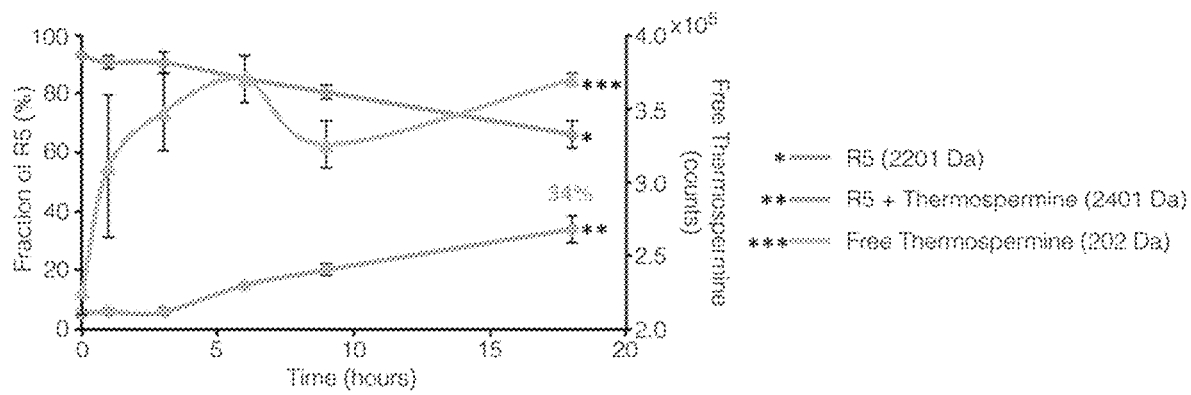
FIG. 5. Propylamination of R5 by Thermospermine Synthase ACL5. A time course graph showing the relative percentages of each R5 species (unmodified and with one thermospermine attached), as well as the synthesis of free thermospermine.

Thermospermine synthase ACL5 from *Arabidopsis thaliana* catalyzes the formation of free thermospermine from S-adenosyl-3-(methylthio)propylamine (decarboxylated SAM) and spermidine. Subsequently, ACL5 can covalently attach thermospermine to R5. The ACL5 gene was optimized for expression in *E. coli*, synthesized, transformed into *E. coli*, expressed, and purified by affinity chromatography. Purified ACL5 was incubated with 100 mM Tris-HCl, pH 7.5, 32 µM SAM, 63 mM spermidine, and 20 µM R5 at 32° C. for one to 16 hours, followed by heat inactivation at 95° C. for 5 minutes. A time course showing the production of free thermospermine and the incorporation of one thermospermine molecule into R5 (FIG. 5) was determined by LC-MS.

Example 5: Generation of Melanin-Modified R5 Peptide

Figure 6A:
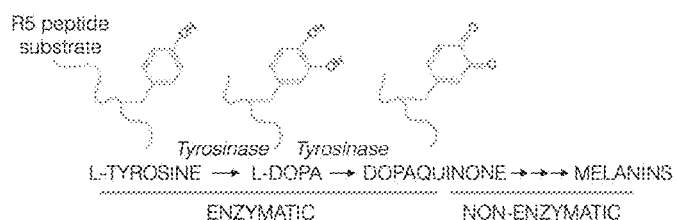
FIGS. 6A-6D. R5-melanin formation by Tyrosinase.

Tyrosinase is an enzyme responsible for melanin synthesis via the oxidation of free tyrosine (FIG. 6A). Tyrosinase from mushrooms (Sigma T3824) was reconstituted in water at varying concentrations (0-1,000 U/mL) and incubated with R5 at room temperature for 16 hours. The R5 peptide was recombinantly expressed in *Escherichia coli* (*E. coli*) and purifying the peptide by affinity and size exclusion chromatography. The purified peptide was lyophilized and then resuspended in water at known concentrations (50 uM-3 mM).

Figure 6B:
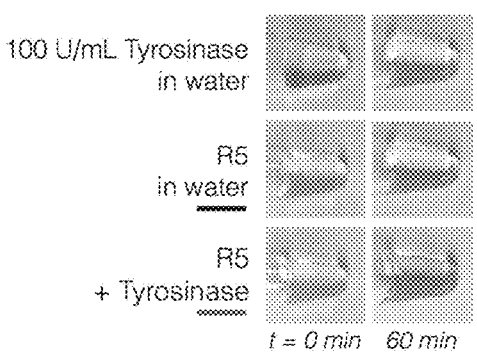
Figure 6C:
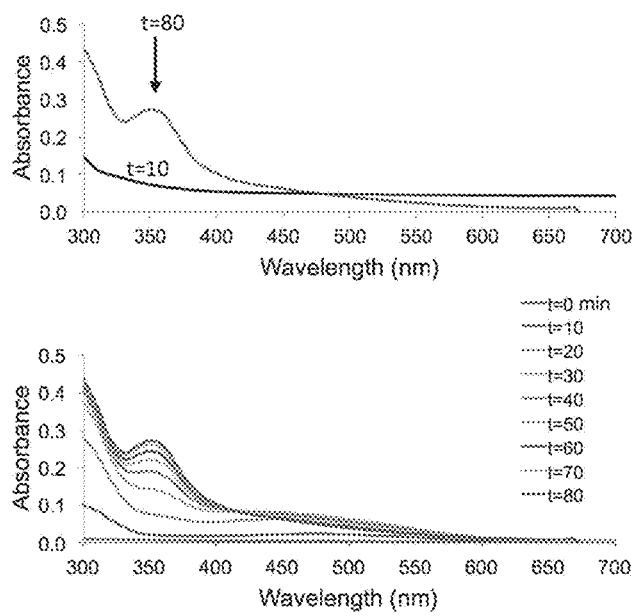
Figure 6D:
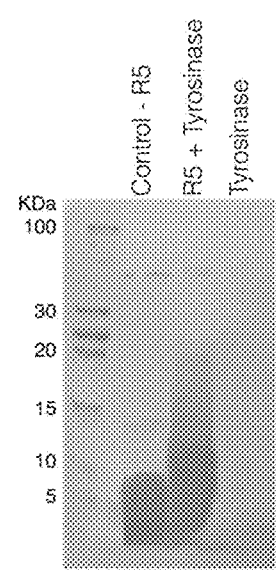

A time course was generated showing the production of oxidized R5 (FIGS. 6B-6C) and the subsequent spontaneous formation of R5 polymers, or a version of melanin made from R5 (FIG. 6D). Formation of melanin was verified by spectroscopy (FIGS. 6B-6C)—an observed increase in absorbance at 350 nm (characteristic wavelength of melanin)—and by SDS-PAGE analysis and Coomassie staining (FIG. 6D), These results demonstrate the polymerization of the R5 peptides. Additional characterization by QTOF confirmed the mixed presence of R5 monomers and polymers, but could not determine the relative ratios or the size of the polymers.

Additionally, a three plasmid system was constructed to co-express R5 and two Tyrosinase enzymes (melA and melC1) from *Streptomyces antibioticus* in *E. coli* (della-Cioppa G., et al., Biotechnology, 1990 July; 8(7): 634-38). This system facilitates the induction of R5 polymerization in vivo and the subsequent purification of R5 polymers from *E. coli*.

Example 6: Generation of Myristoylated R5 Peptide

Figure 7:
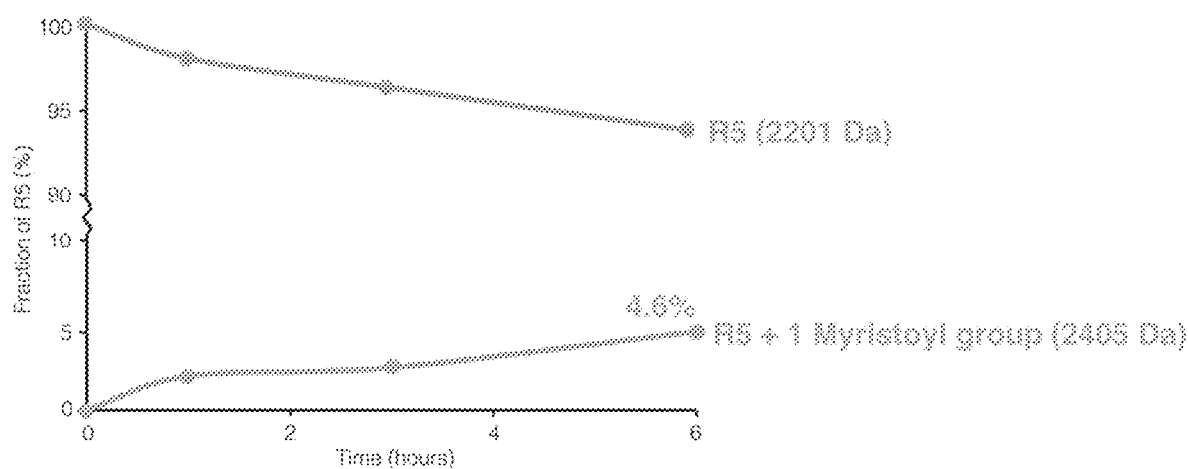
FIG. 7. Myristoylation by N-Myristoyltransferase 1. A time course graph showing the relative percentages of each R5 species (unmodified and with one myristoyl group attached).

The human NMT1 gene was optimized for expression in *E. coli*, synthesized, transformed into *E. coli*, expressed, and purified by affinity chromatography. Purified N-myrisotyl-transferase 1 (NMT1) was incubated with myristoyltransferase buffer (30 mM Tris-HCl, pH 7.5, 0.5 mM EDTA, 0.5 mM EGTA, 1.0% Triton X-100, 4.5 mM 2-mercaptoethanol), 200 µM myristoyl-CoA, and 200 µM R5 at 25° C. for one to six hours, followed by heat inactivation at 95° C. for 5 minutes. A time course showing the incorporation of one myristoyl group was determined by LC-MS (FIG. 7).

Example 7: Generation of Hypusine-Modified R5 Peptide

Figure 8:
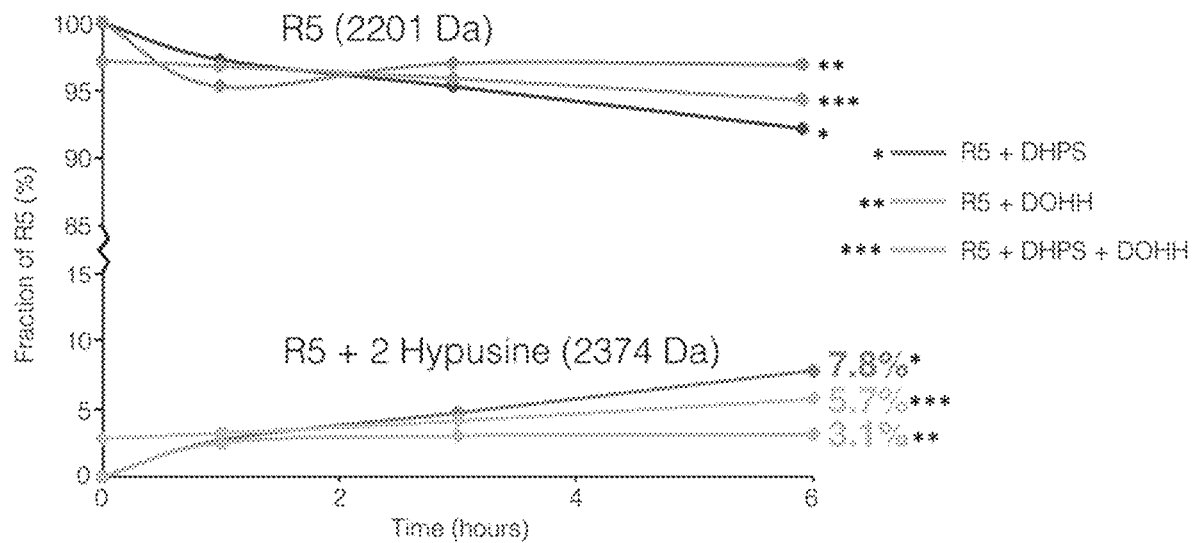
FIG. 8. Hypusination by DHPS and DOHH. A time course graph showing the relative percentages of each R5 species (unmodified and with two hypusine groups attached) in the presence of deoxyhypusine synthase (DHPS) and deoxyhypusine hydroxylase (DOHH). No intermediates or presence of one hypusine residue were detected.

The human DHPS gene was optimized for expression in *E. coli*, synthesized, transformed into *E. coli*, expressed, and purified by affinity chromatography. Purified deoxyhypusine synthase (DHPS) was incubated with hypusination buffer (200 mM glycine, pH 9.4, 1 mM DTT, 0.5 mM NAD+, 375 µM BSA), 20 mM spermidine, 200 µM R5 at 37° C. for one to 6 hours, followed by heat inactivation at 95° C. for 5 minutes. A time course showing the conversion of two lysine to hypusine residues was determined by LC-MS (FIG. 8). No intermediates or presence of one hypsine residue were detected.

The human DOHH gene was optimized for expression in *E. coli*, synthesized, transformed into *E. coli*, expressed, and purified by affinity chromatography. Purified deoxyhypusine hydroxulase (DOHH) was incubated with hypusination buffer (200 mM glycine, pH 9.4, 1 mM DTT, 0.5 mM NAD+, 375 µM BSA), 20 mM spermidine, 200 µM R5 at 37° C. for one to 6 hours, followed by heat inactivation at 95° C. for 5 minutes. A time course showing the conversion of two lysine to hypusine residues was determined by LC-MS (FIG. 8). No intermediates or presence of one hypsine residue were detected.

Example 8: Other Modifications of R5 Peptide

Additional enzymes were tested for enzymatic activity against R5 but showed no resulting modifications (TABLE 1). Additional potential modifying enzymes are listed in TABLE 2.

TABLE 1

List of modifying enzymes that were tested against R5 but resulted in no modifications.

| Enzyme Name | Organism | Modification Type |
|---|---|---|
| BRSK2 | *Homo sapiens* | Phosphorylation |
| JMJD6 | *Auxenochlorella prototheocoides* | Hydroxylation |
| JMJD6 | *Nannochloropsos gaditana* | Hydroxylation |
| THAOC_04424 | *Thalassiosira oceanica* | Hydroxylation |
| THAOC_27572 | *Thalassiosira oceanica* | Hydroxylation |
| vopS | *Vibrio parahaemolyticus* serotype O3:K6 | Adenylylation |
| BirA | *Escherichia coli* | Biotinylation |
| GALNT1 | *Homo sapiens* | Glycosylation |
| OGT | *Homo sapiens* | Glycosylation |
| POMT1 | *Homo sapiens* | Glycosylation |
| LplA | *Escherichia coli* | Lipidation |
| LipB | *Escherichia coli* | Lipidation |
| LIPT1 | *Escherichia coli* | Lipidation |
| NMT2 | *Homo sapiens* | Lipidation |

TABLE 2

List of potential R5 modifying enzymes.

| Enzyme Name | Organism | Modification Type |
|---|---|---|
| gi_71042599 | Eukaryotic | Methyltransferase |
| gi_512853798 | Eukaryotic | Methyltransferase |
| gi_16754879 | Eukaryotic | Methyltransferase |
| THAPSDRAFT_20746 | T. pseudonana | hypothetical protein (methyltransferase) |
| THAPSDRAFT_32876 | T. pseudonana | hypothetical protein (methyltransferase) |
| THAPSDRAFT_21274 | T. pseudonana | hypothetical protein (methyltransferase) |
| THAPSDRAFT_11244 | T. pseudonana | hypothetical protein (methyltransferase) |
| THAPSDRAFT_24355 | T. pseudonana | hypothetical protein (methyltransferase) |
| THAPSDRAFT_30620 | T. pseudonana | hypothetical protein (methyltransferase) |
| THAPSDRAFT_263816 | T. pseudonana | hypothetical protein (methyltransferase) |
| THAPS_41291 | T. pseudonana | CAM1 - calmodulin (methyltransferase) |
| THAPSDRAFT_23288 | T. pseudonana | hypothetical protein (methyltransferase) |
| cffcpA-2 | C. fusiformis | chlorophyll related (methyltransferase) |
| SIT4A | C. fusiformis | silicon transporter (methyltransferase) |
| SIT2 | C. fusiformis | silicon transporter (methyltransferase) |
| DSK1 | C. fusiformis | spindle kinesin 1 (methyltransferase) |
|  | C. fusiformis | nitrate reductase (methyltransferase) |
| MAP2 | T. pseudonana | methionine aminopeptidase 2 (methyltransferase) |
| RPC25 | T. pseudonana | RNA pol III (methyltransferase) |
| THAPSDRAFT_35182 | T. pseudonana | set domain-containing protein (methyltransferase) |
| THAPSDRAFT_268872 | T. pseudonana | set-domain-containing protein (methyltransferase) |
| THAPSDRAFT_22056 | T. pseudonana | hypothetical protein (methyltransferase) |
| THAPSDRAFT_3607 | T. pseudonana | hypothetical protein (methyltransferase) |
| THAPSDRAFT_bd1835 | T. pseudonana | hypothetical protein (methyltransferase) |
| THAPSDRAFT_11154 | T. pseudonana | hypothetical protein (methyltransferase) |
| THAPSDRAFT_11069 | T. pseudonana | hypothetical protein (methyltransferase) |
| THAPSDRAFT_268872 | T. pseudonana | hypothetical protein (methyltransferase) |
| THAPSDRAFT_23212 | T. pseudonana | hypothetical protein (methyltransferase) |
| THAPSDRAFT_5135 | T. pseudonana | hypothetical protein (methyltransferase) |
| THAPSDRAFT_23725 | T. pseudonana | hypothetical protein (methyltransferase) |
| MET | T. pseudonana | Methyltransferase |
| rbcMT | P. tricornutum | Methyltransferase |
| PHATRDRAFT_55013 | P. tricornutum | Methyltransferase |
| PHATRDRAFT_51541 | P. tricornutum | Methyltransferase |
| PHATRDRAFT_46484 | P. tricornutum | hypothetical protein (methyltransferase) |
| PHATRDRAFT_47888 | P. tricornutum | hypothetical protein (methyltransferase) |
| PHATDRAFT_45376 | P. tricornutum | hypothetical protein (methyltransferase) |
| PHATRDRAFT_6698 | P. tricornutum | hypothetical protein (methyltransferase) |
| PHATRDRAFT_42601 | P. tricornutum | hypothetical protein (methyltransferase) |
| PHATRDRAFT_3251 | P. tricornutum | hypothetical protein (lysyl hydroxylase) |
| PHATRDRAFT_49314 | P. tricornutum | hypothetical protein (lysyl hydroxylase) |
| THAPSDRAFT_8036 | T. pseudonana | hypothetical protein (lysyl hydroxylase) |
| THAPSDRAFT_7775 | T. pseudonana | hypothetical protein (lysyl hydroxylase) |
| THAOC_27572 | T. oceanica | hypothetical protein (lysyl hydroxylase) |
| THAOC_04424 | T. oceanica | hypothetical protein (lysyl hydroxylase) |
| THAPSDRAFT_34059 | T. pseudonana | Kinase |
| THAPS_35643 | T. pseudonana | Kinase |
| LCYB | P. tricornutum | lycopene beta cyclase (methyltransferase?) |
| THAPSDRAFT_270357 | T. pseudonana | hypothetical protein |
| THAPSDRAFT_13556 | T. pseudonana | hypothetical protein |
| LAT2 | T. pseudonana | Acetyltransferase |
| THAPSDRAFT_2538 | T. pseudonana | Phosphatase |
| THAPSDRAFT_2540 | T. pseudonana | hypothetical protein (acetyltransferase) |
| THAPSDRAFT_21409 | T. pseudonana | hypothetical protein (methyltransferase) |
| THAPSDRAFT_2711 | T. pseudonana | hypothetical protein |
| THAPSDRAFT_3500 | T. pseudonana | hypothetical protein (glycosyl transferase) |
| THAPSDRAFT_33728 | T. pseudonana | hypothetical protein (kinase) |
| THAPSDRAFT_22506 | T. pseudonana | hypothetical protein |
| THAPSDRAFT_8998 | T. pseudonana | hypothetical protein (methyltransferase) |
| THAPSDRAFT_17140 | T. pseudonana | hypothetical protein (propylamination) |
| THAPSDRAFT_21371 | T. pseudonana | Spermidine synthase |
| THAPSDRAFT_23207 | T. pseudonana | hypothetical protein (propylamination) |
| THAPSDRAFT_24273 | T. pseudonana | hypothetical protein (propylamination) |
| THAPSDRAFT_24769 | T. pseudonana | hypothetical protein (propylamination) |
| THAPSDRAFT_261161 | T. pseudonana | hypothetical protein (propylamination) |
| THAPSDRAFT_262580 | T. pseudonana | hypothetical protein (propylamination) |
| THAPSDRAFT_264237 | T. pseudonana | hypothetical protein (propylamination) |
| THAPSDRAFT_264730 | T. pseudonana | hypothetical protein (propylamination) |
| THAPSDRAFT_267946 | T. pseudonana | hypothetical protein (propylamination) |
| THAPSDRAFT_269901 | T. pseudonana | Thermospermine synthase |
| THAPSDRAFT_30691 | T. pseudonana | Spermine synthase |
| ACL5 | A. thaliana | Thermospermine synthase |
| TPS_41289 | T. pseudonana | Thermospermine synthase? |
| POFUT1 (GDP-frucose protein O-fucosyltransferase 1) | Homo sapiens | Glycosylation |
| POFUT2 (GDP-frucose protein O-fucosyltransferase 2) | Homo sapiens | Glycosylation |
| POMT1 (Protein O-mannosyl-transferase 1) | Homo sapiens | Glycosylation |
| PLOD1 (Procollagen-lysine, 2-oxoglutarate 5-dioxygenase 1) | Homo sapiens | Glycosylation |
| TPST1 (Protein-tyrosine sulfotransferase 1) | Homo sapiens | Sulfonation |
| TPST2 (Protein-tyrosine sulfotransferase 2) | Homo sapiens | Sulfonation |
| ELP3 | Saccharomyces cerevisiae | Acetylation |
| HAT1 | Saccharomyces cerevisiae | Acetylation |

TABLE 2-continued

List of potential R5 modifying enzymes.

| Enzyme Name | Organism | Modification Type |
|---|---|---|
| GCN5 | Homo sapiens | Acetylation |
| KAT2A | Homo sapiens | Acetylation |
| p300 (E1A-associated protein 300 kDa) | | Acetylation |
| MOZ, YBF2/Sas3, Sas2, Tip60 = MYST family | | Acetylation |
| Morf | | Acetylation |
| Crebbp | | Acetylation |
| Lysyl Hydroxylase 3 (LH3) | | Hydroxylation |
| Lysyl Hydroxylase 2 (LH2) | | Hydroxylation |
| Lysyl Hydroxylase 1 (LH1) | | Hydroxylation |
| Ca2+/calmodulin dependent protein kinase II | | Phosphorylation |
| DAP Kinase | | Phosphorylation |
| GSK3α | Homo sapiens | Phosphorylation |
| GSK3β | Homo sapiens | Phosphorylation |
| TPS_41289 | Thalassiosira psuedonana | Propylamination |
| TPS_108361 | Thalassiosira psuedonana | Propylamination |
| SPDS | | Propylamination |
| SPMS | | Propylamination |
| tSPMS | | Propylamination |
| PMT | | Propylamination |
| SpeD | | Propylamination |

Example 9: Altered Silica Morphology Using R5-Melanin

Figure 9:
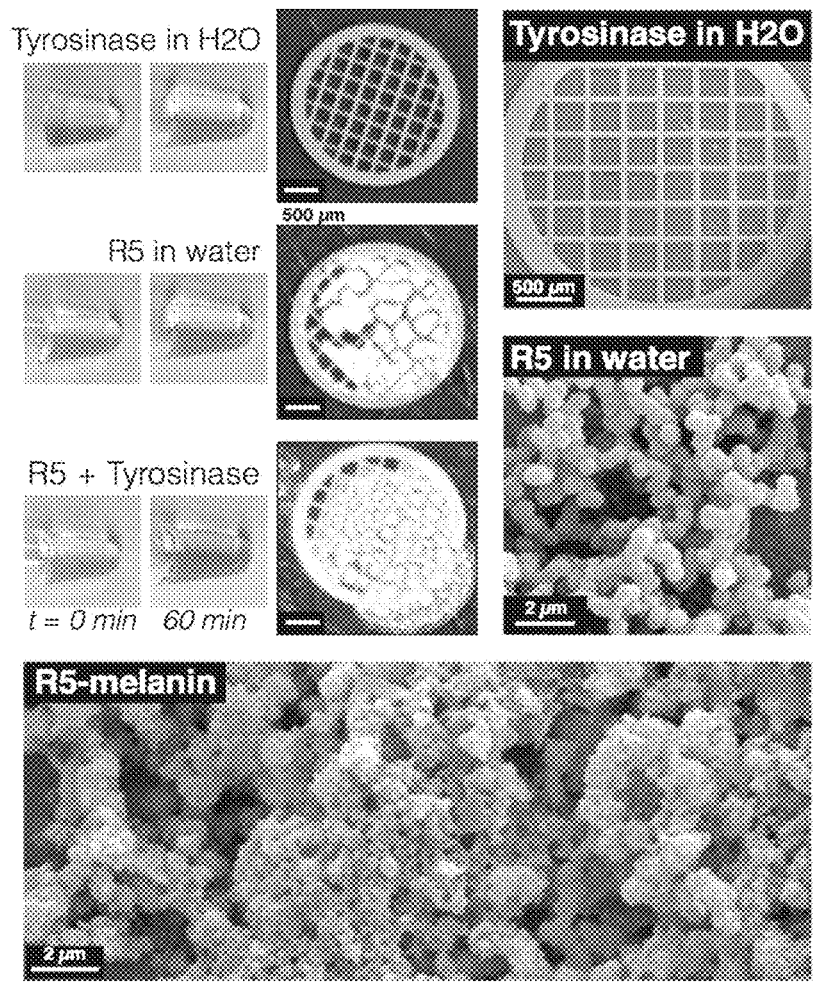
FIG. 9. R5-melanin silica precipitation. Unmodified R5 peptides precipitated highly uniform silica spheres that appeared white (R5 in water). R5-melanin precipitated brown, porous silica.

R5-melanin (polymerized R5) was used to precipitate amorphous silicon dioxide (silica). First, R5 polymers were enriched for from the mixed monomer/polymer sample by size exclusion chromatography. The silica precipitation reaction was performed as previously published (Kröger N., et al., Science, 1999 Nov. 5; 286(5442): 1129-32), while using R5-melanin in place of unmodified R5 peptides. Briefly, silicic acid was created by hydrolyzing tetramethyl orthosilicate (TMOS) in hydrochloric acid. Silicic acid was then added to R5-melanin in a phosphate buffered solution at a 1:10 ratio. Silica precipitation occurred spontaneously at room temperature. After 10 minutes the particles were pelleted and washed with water and dried. The dried silica was visibly brown to the naked eye, indicating that the melanin was embedded in the silica. When analyzed by scanning electron microscope (SEM) the silica morphology appeared porous (FIG. 9). This melanin-embedded silica can be generated in less than two hours.

Figure 10A:
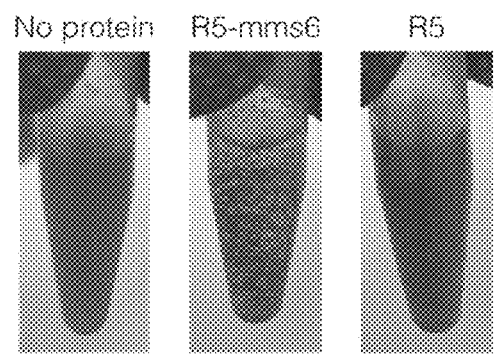
FIGS. 10A-10B. In vitro synthesis of silica-coated iron oxide nanoparticles using R5-Mms6.

Example 10: R5-Mms6 for In Vitro Silica-Coated Iron Oxide Nanoparticle Synthesis A DNA fragment encoding for the R5 peptide (5'-ATGTCCTCCAAAAAATCTGGTTCATATTCCGGCTCT AAAGGCAGTAAACGTCGTATCTTA-3') (SEQ ID NO: 90) was fused to the N-terminal of the mms6 gene, which is an iron binding protein used to regulate magnetosome crystal morphology. R5-mms6 was cloned into a pMB1 plasmid vector, and transformed into *E. coli*, and cultured in liquid media. Recombinant R5-Mms6 was purified from *E. coli* by affinity and size exclusion chromatography and subsequently lyophilized. R5-Mms6 then was used to precipitate iron oxide nanoparticles in vitro by the partial oxidation method (FIG. 10A) (Amemiya Y., et al., Biomaterials, 2007 December; 28(35): 5381-89).

Figure 10B:
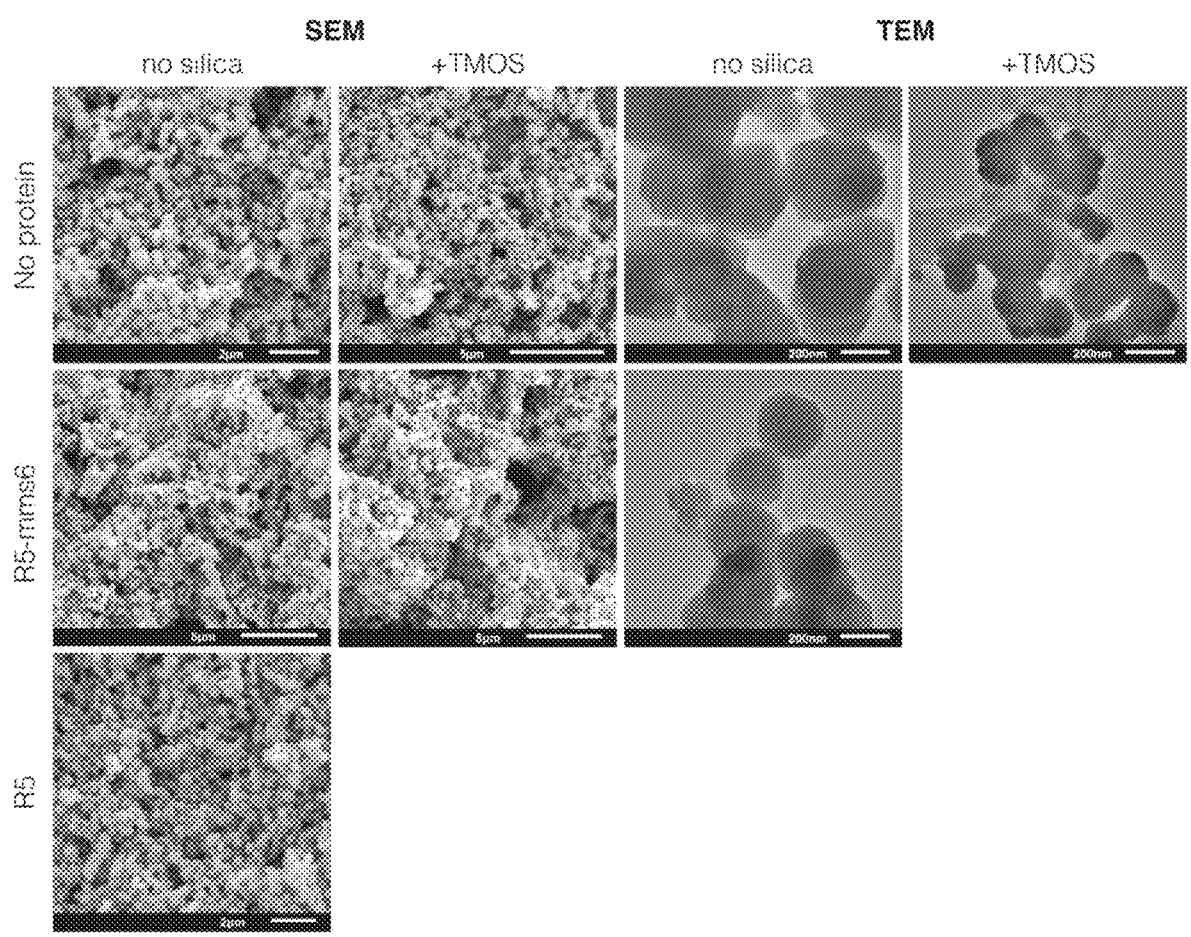
Figure 11A:
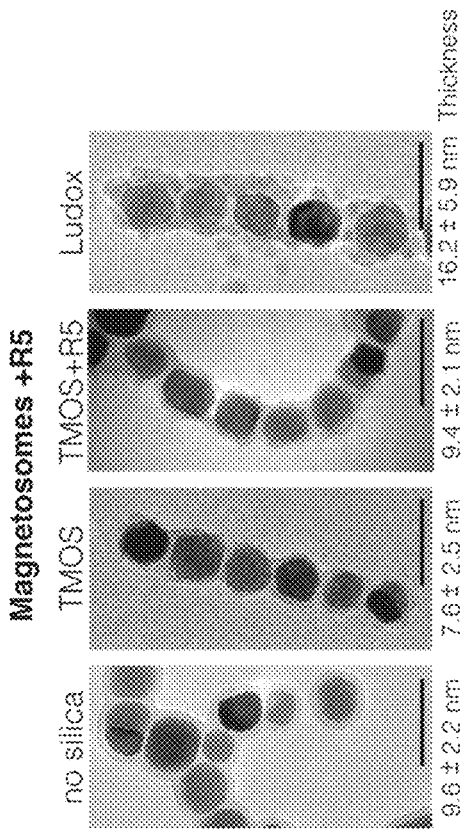
FIGS. 11A-11D. In vitro synthesis of silica-coated magnetosomes using R5-MamC. Genetically engineered *M. magneticum* produce magnetosomes displaying R5 on the surface. Magnetosomes were coated with silica through the addition of silicic acid (either TMOS or Ludox HS-30 as the silica source).
Figure 11B:
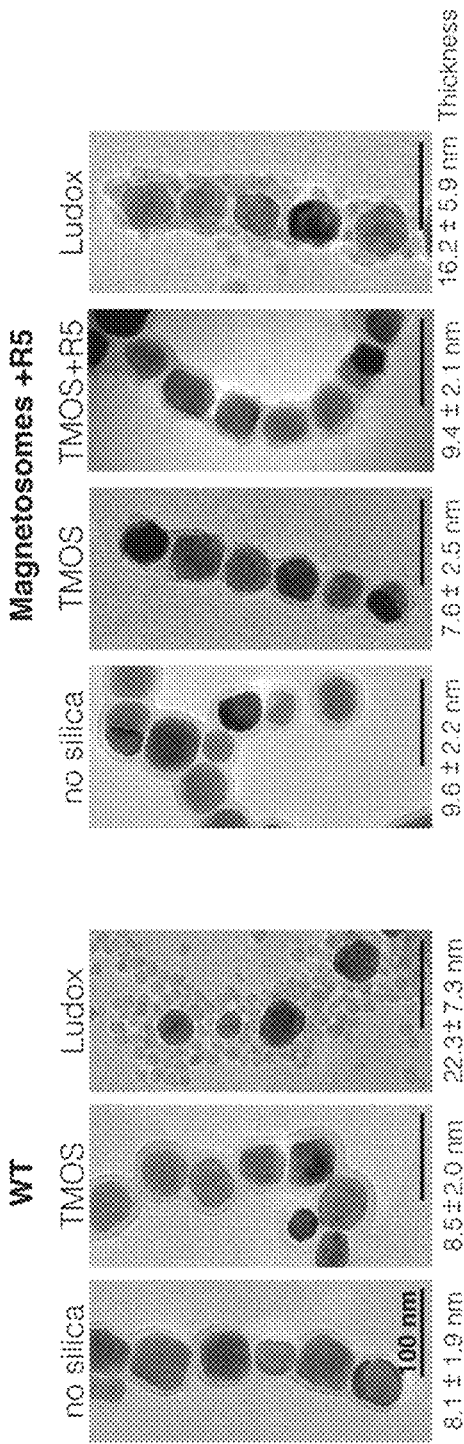
Figure 11C:
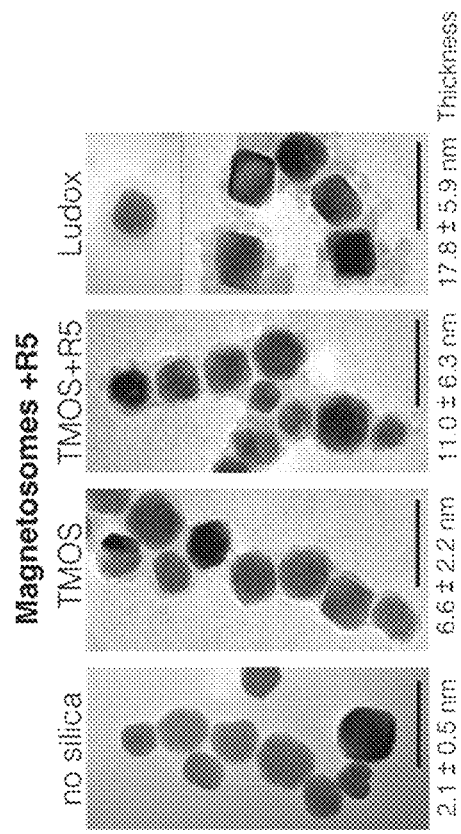
Figure 11D:
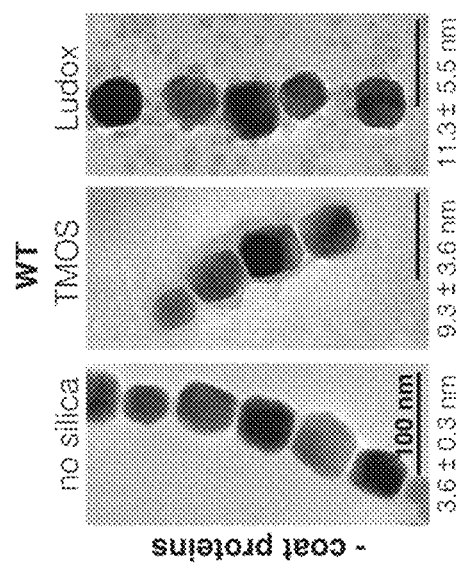

Silica coating of the R5-Mms6 synthesized iron nanoparticles was performed by first hydrolyzing TMOS in hydrochloric acid to produce silicic acid. The nanoparticles were then incubated with 100 mM silicic acid in a phosphate buffered solution (FIG. 10B). In some samples, an additional 1 mM R5 peptide was added in the reaction (FIG. 10B). By energy-dispersive X-ray spectroscopy (EDS) we determined that the nanoparticles were composed of iron oxide ($Fe_3O_4$). The addition of TMOS and R5 resulted in approximately 5% silicon dioxide.

Example 11: R5-MamC for Combination In Vivo/In Vitro Silica-Coated Magnetosome (Magnetic Nanoparticle) Synthesis A DNA fragment encoding for R5 peptide (5'-TCCTCCAAAAAATCTGGTTCATATTCCGGCTCTAAAGG CAGTAAACGTCGTATCTTA-3') (SEQ ID NO: 91) was fused to the C-terminal of the mamC gene, which is a magnetosome surface protein. The mamC-R5 gene was cloned into a pMGA plasmid vector, and conjugated into *Magnetospirillum magneticum*, and cultured in liquid media. The R5-displaying magnetosomes were purified from the recombinant *M. magneticum* by French Press and bar-magnet, washed with HEPES-EDTA and 2M NaCl, and finally resuspended in deionized water or HEPES (pH7.4) buffer.

Figure 13:
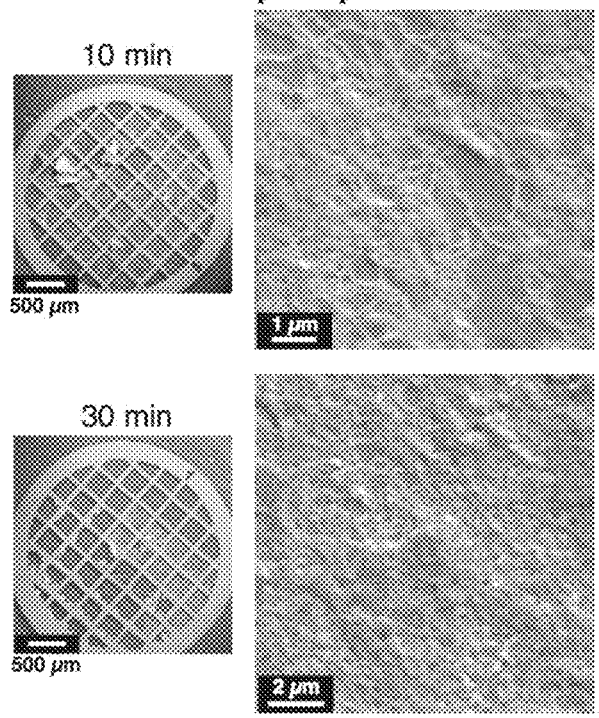
FIG. 13. SEM analysis of R5-MamC magnetosomes silica precipitation.
Figure 14:
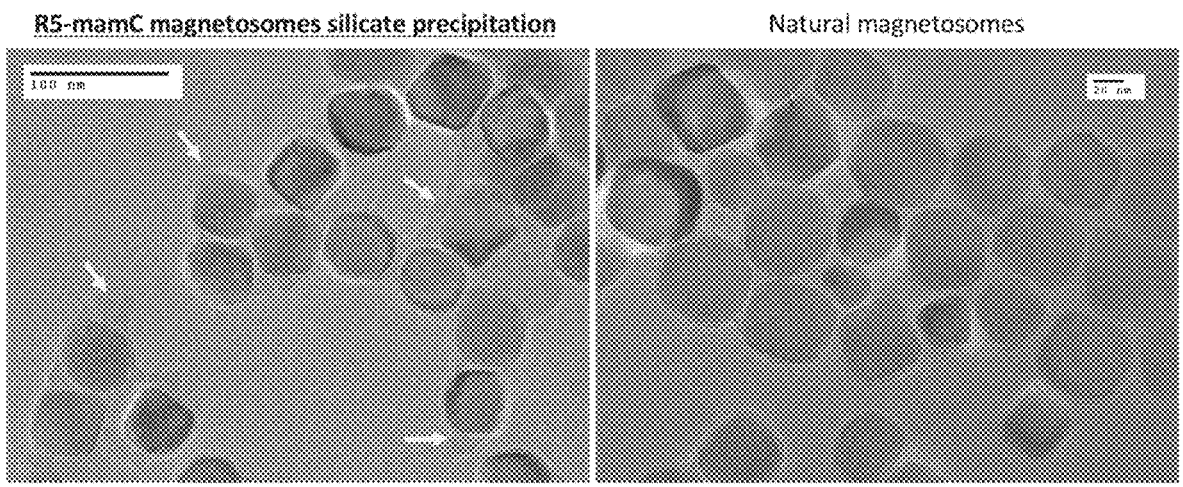
FIG. 14. TEM analysis of R5-MamC magnetosomes silica precipitation.

The R5-displaying magnetosomes were resuspended in a phosphate buffered solution and mixed with silicic acid at room temperature. Silica precipitation was analyzed after 30 minutes. The dried material appeared black to the naked eye. By TEM, magnetosome chains coated in a layer of silica were observed (FIG. 11 and FIG. 13). By energy-dispersive X-ray spectroscopy (EDS) it was determined that the samples contain approximately 50-80% iron oxide ($Fe_3O_4$) and 5-10% silicon dioxide. By TEM, silicate coating on the surface of magnetosomes was observed (FIG. 14).

Example 12: CNT-Binding Magnetosomes

DNA fragments encoding for carbon-nanotube-binding peptides (CNT1, 5'-CACTCCTCCTACTGGTA CGCCTT-CAACAACAAGACC-3' (SEQ ID NO: 92) or CNT2, 5-'GACTCCCCGCACACCGAGCTGCCG-3') (SEQ ID NO: 93) were fused to the C-terminal of the mamC gene. MamC-CNT and MamC-CNT2 genes were cloned into pMGA plasmid vector, conjugated into *M. magneticum* and cultured in liquid media. The magnetosomes were purified from each recombinant *M. magneticum* by French Press and bar-magnet, washed with HEPES-EDTA and 2M NaCl, and finally resuspended in deionized water.

TABLE 3

| Metal Binding Peptides to Combine/Fuse with R5. | | | | |
|---|---|---|---|---|
| Peptide Name | Sequence | SEQ ID NO | Metal(s) | Ref. |
| DBAD1STEARATTL TACDAY | | 35 | Al | Adams B. L., et al., Adv. Mater. 2013 Sep 6; 25(33): 4530-91. |

TABLE 3-continued

Metal Binding Peptides to Combine/Fuse with R5.

| Peptide Name | Sequence | SEQ ID NO | Metal(s) | Ref. |
|---|---|---|---|---|
| A1-S1 | VPSSGPQDTRTT | 36 | Al | Zuo R., et al., Appl. Microbiol. Biotechnol. 2005 Sep; 68(4): 505-9. |
| A1-S2 | YSPDPRPWSSDY | 37 | Al | Zuo R., et al., Appl. Microbiol. Biotechnol. 2005 Sep; 68(4): 505-9. |
| BT1 | HQPANDPSWYTG | 38 | BaTiO$_3$ | Ahmad G., et al., J. Am. Chem. Soc. 2008 Jan 9; 130(1): 4-5. |
| BT2 | NTISGLRYAPHM | 39 | BaTiO$_3$ | Ahmad G., et al., J. Am. Chem. Soc. 2008 Jan 9; 130(1): 4-5. |
| A7 | CNNPMHQNC | 40 | ZnS | Flynn C. E., et al., J. Mater. Chem. 2003; 13(10): 2414-21. |
| Z8 | LRRSSEAHNSIV | 41 | ZnS | Flynn C. E., et al., J. Mater. Chem. 2003; 13(10): 2414-21. |
| J182 | CTYSRLHLC | 42 | CdS | Flynn C. E., et al., J. Mater. Chem. 2003; 13(10): 2414-21. |
| J140 | SLTPLTTSHLRS | 43 | CdS | Flynn C. E., et al., J. Mater. Chem. 2003; 13(10): 2414-21. |
| 5R39 | GRVLAGSSAVSSRPS | 44 | CaCO$_3$ | Li C., et al., Cryst. Growth Des. 2002; 2(5): 387-93. |
| 4R12 | AYGSSGFYSASFTPR | 45 | CaCO$_3$ | Li C., et al., Cryst. Growth Des. 2002; 2(5): 387-93. |
| AG-4 | NPSSLFRYLPSD | 46 | Ag | Naik R. R., et al., Adv. Funct. Mater. 2004; 14(1): 25-30. |
| AG-P35 | WSWRPTPHVVT | 47 | Ag | Naik R. R., et al., Adv. Funct. Mater. 2004; 14(1): 25-30. |
| Col-P10 | HYPTLPGSSTT | 48 | Co | Naik R. R., et al., Adv. Funct. Mater. 2004; 14(1): 25-30. |
| CN225 | RHTDGLRRIAAR | 49 | Cu(II) | Thai C. K., et al., Biotechnol. Bioengin. 2004 Jul 20; 87(2): 129-37. |
| CN44 | NTVWRLNSSCGM | 50 | Cu(II) | Thai C. K., et al., Biotechnol. Bioengin. 2004 Jul 20; 87(2): 129-37. |
| CN179 | RIGHGRQIRKPL | 51 | ZnO | Thai C. K., et al., Biotechnol. Bioengin. 2004 Jul 20; 87(2): 129-37. |
| CN146 | MRHSSSGEPRLL | 52 | ZnO | Thai C. K., et al., Biotechnol. Bioengin. 2004 Jul 20; 87(2): 129-37. |
| HG12 | HGGGHGHGGGHG | 53 | Cu(II), Ni(II) | Banerjee I. A., et al., Proc. Natl. Acad. Sci. U.S.A. 2003 Dec 9; 100(25): 14678-82. |
| HG6 | HGGGHG | 54 | Cu(II), Ni(II) | Pappalardo G., et al., New J. Chem. 2002; 26(5): 593-600. |
| Ge8 | SLKMPHWPHLLP | 55 | GeO$_2$ | Dickerson M. B., et al., Chem. Commun, 2004 Aug 7; (15): 1776-77. |
| Ge34 | TGHQSPGAYAAH | 56 | GeO$_2$ | Dickerson M. B., et al., Chem. Commun. 2004 Aug 7; (15): 1776-77. |
| Gold-binding peptide a | LKAHLPPSR | 57 | Au | Nam K. T., et al., Science. 2006 May 12; 312(5775): 885-88. |
| Gold-binding peptide b | AHHAHAAD | 58 | Au | Djalali R., et al., J. Am. Chem. Soc. 2003 May 14; 125(19): 5873-79. |
| MS-S1 | ATIHDAFYSAPE | 59 | Fe | Zuo R., et al., Appl. Microbiol. Biotechnol. 2005 Sep; 68(4): 505-9. |
| RE-1 | ACTARSPWICG | 60 | Lanthide oxides: $Y_2O_3$, $CeO_2$, $Yb_2O_3$, $Nd_2O_3$, $Er_2O_3$, $La_2O_3$, $Eu_2O_3$, $Pr_6O_{11}$, $Tb_4O_7$, $Gd_2O_3$ | Zhang Y., et al., Nat. Mater. 2012 Sep; 11(9): 817-26. |
| Ag-22 | TVPPKAPRSSDL | 61 | Ag | Bassindale A. R., et al., Chem. Commun. 2007 Jul 28; (28): 2956-58. |
| Ag-28 | LTRPNHGNTVDT | 62 | Ag | Bassindale A. R., et al., Chem. Commun. 2007 Jul 28; (28): 2956-58. |
| Pt-41 | SRLTHSNYATPT | 63 | Pt | Bassindale A. R., et al., Chem. Commun. 2007 Jul 28; (28): 2956-58. |
| Pt-14 | EHTNPILSHTHN | 64 | Pt | Bassindale A. R., et al., Chem. Commun. 2007 Jul 28; (28): 2956-58. |

TABLE 3-continued

Metal Binding Peptides to Combine/Fuse with R5.

| Peptide Name | Sequence | SEQ ID NO | Metal(s) | Ref. |
|---|---|---|---|---|
| Pt-1.2 | QSFSTNVLHTHH | 65 | Pt | Bassindale A. R., et al., Chem. Commun. 2007 Jul 28; (28): 2956-58. |
| HPGAHHPGAH | | 66 | Pt | Tsiveriotis P. and Hadjiliadis N., Coord. Chem. Rev. 1999; 171-84. |
| AG3 | AYSSGAPPMPPF | 67 | Ag | Naik R. R., et al., Nat. Mater. 2002 Nov; 1(3): 169-72. |
| AG4 | NPSSLFRYLPSD | 68 | Ag | Naik R. R., et al., Nat. Mater. 2002 Nov; 1(3): 169-72. |
| dTi-1 (RKK) | RKKRKKRKKRKKGGGW | 69 | TiO$_2$ | Dickerson M. B., et al., Chem. Mater. 2008; 20(4): 1578-84. |
| Ti-1 | RKKRTKNPTHKLPFFW | 70 | TiO$_2$ | Dickerson M. B., et al., Chem. Mater. 2008; 20(4): 1578-84. |
| PG-7 | TMGANLGLKWPV | 71 | ZnO | Golec P., et al., J. Nanopar. Res. 2012. 14(11): 1218. |
| ZnO-1a | EAHVMHKVAPRP | 72 | ZnO | Umetsu M., et al., Adv. Mater. 2005; 17(21): 2571-75. |
| ZnO-1b | HVNLHS | 73 | ZnO | Okochi M., et al., Acta. Biomater. 2010 Jun;. 6(6): 2301-06. |
| ZnO-2 | RCARRY | 74 | ZnO | Okochi M., et al., Acta. Biomater. 2010 Jun;. 6(6): 2301-06. |
| ZnO-3 | HYQSNW | 75 | ZnO | Okochi M., et al., Acta. Biomater. 2010 Jun;. 6(6): 2301-06. |
| ZnO-4 | HWFHPR | 76 | ZnO | Okochi M., et al., Acta. Biomater. 2010 Jun;. 6(6): 2301-06. |
| HA6-1 | SVSVGMKPSPRP | 77 | Hydroxy-apatite (Ca$_5$(PO$_4$)$_3$(OH)) | Roy M. D., et al., Adv. Mater. 2008; 20(10): 1830-36. |
| HABP1 | CMLPHHGAC | 78 | Hydroxy-apatite (Ca$_5$(PO$_4$)$_3$(OH)) | Gungormus M., et al., Biomacromolecules. 2008 Mar; 9(3): 966-73. |
| HABP2 | CNPGFAQAC | 79 | Hydroxy-apatite (Ca$_5$(PO$_4$)$_3$(OH)) | Gungormus M., et al., Biomacromolecules. 2008 Mar; 9(3): 966-73. |

Example 13: Silica-Coated DNA Nanostructures (DNA Origami) Using R5

Coating DNA nanostructures with silica to reduce biological immune responses is an active area of research. Using R5 to precipitate silica coatings may enable thinner coatings than alternative chemical methods and may allow for DNA nanostructure morphologies to be retained even after the coatings, thereby allowing the DNA structure to remain functional after being coated with silica. Other methods of generated these structures results in silica that completely engulfs the nanostructure.

Figure 12:
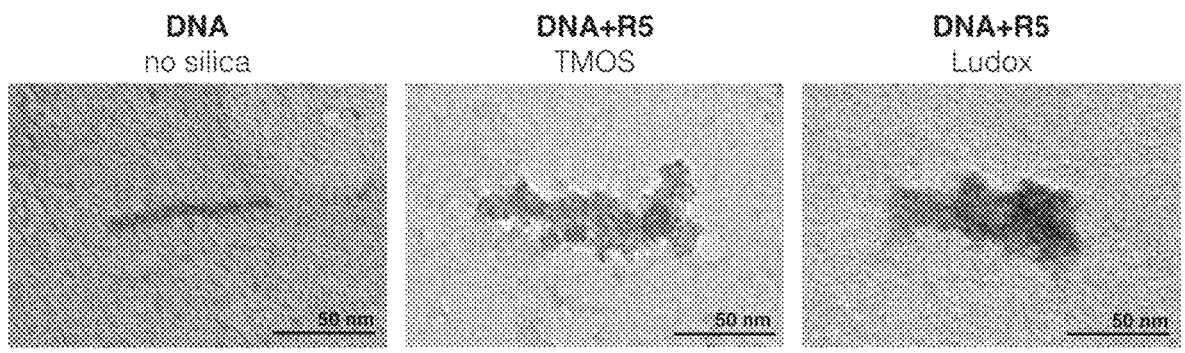
FIG. 12. Silica-coated DNA nanostructures using R5. A six-helix bundle DNA nanostructure (6 nm diameter, 80 nm length) was coated with a layer of silica when in the presence of R5.

A six-helix bundle DNA nanostructure was folded as previously published (Castro C. E., et al., Nat. Methods, 2011 March; 8(3): 221-29). The DNA nanostructure was then incubated with R5 in a magnesium and phosphate buffered solution for 30 minutes at room temperature. The silica precipitation reaction was initiated by adding 100 mM of hydrolyzed silicic acid (TMOS or Ludox HS-30 silica sources) to the solution. After 30 minutes the sample was prepared for TEM. TEM images indicated a layer of silica around the DNA structure (FIG. 12).

Example 14: Photonic Materials Using R5

Previously described methods of synthesizing synthetic opals can take up to a year (usually seven months) and require high temperatures (800-1150° C.) (Filin S. V., et al., Australian Gemmologist, 2002 January; 21: 278-282; U.S. Pat. No. 4,703,020; P.C.T. App. No. PCT/IN2005/000033). The methods described herein are capable of synthesizing opals at room temperature and over the course of days or less.

Three methods are being explored to order the silica particles produced by unmodified R5 into organized 2D or 3D layered materials to control the optical properties (e.g. opalescence) beyond the light absorption from the polymerized R5. First, unmodified R5 can be used to precipitate silica spheres in solution (per the standard process). The template surface material (e.g. silicon wafer) can then be dipped into the solution. Upon removing the template surface from the solution, the silica spheres should self-organize into a layer on the surface.

Second, layer-by-layer adsorption can be explored (Clark S. and Hammon P., Adv. Mater., 1998 December; 10(18): 1515-19), where a layer of R5 peptide is absorbed onto a silicon wafer surface. The formation of silica spheres on the surface can be tested by submerging the R5-coated layer into a phosphate buffered silicic acid solution, as well as introducing additional free R5 peptide into the reaction. Samples can then be analyzed by profilometery to determine R5 layer thickness, and SEM and TEM to visualize any surface morphologies.

Finally, a protein microarray can be used to immobilize R5 on a surface. A similar process to the layer-by-layer approach can be used to form silica spheres on the surface.

Example 15: Additional Applications

Post-translational modifications to R5 may be able alter the silica morphology (e.g. size, shape, porosity) that is produced in a controlled fashion. Combining multiple modifications on R5 may enable the synthesis of more complex silica structures. Potential applications for these materials include: customizable silica materials, biomedical applications (e.g., drug delivery vehicles, biosensors, bioimaging), catalysis, thermal energy storage, optical fibers, microelectronics, construction materials (e.g. glass), and cosmetics (e.g. abrasive material for face scrubs)

R5-melanin and the R5-melanin-silica may be able to absorb, transduce, and dissipate many forms of energy (e.g. radiation, UV), conduct electrons and ions, or manipulate light. Magnetosomes, or magnetic nanoparticles, are able to absorb electromagnetic wave, generate heat by applying electromagnetic field. Potential applications for these materials (and combinations thereof) include: incorporating R5-melanin with other hydrogel polymers to 3D print macroscale materials for the creation of optical and medical devices; incorporating R5-melanin into bioplastics to yield hard plastic materials with melanin properties; incorporating R5-melanin into fuel cells, green batteries, sensors, or electronics that require electrical conductivity or optical features; using R5-melanin-silica as substrates for catalytic reactions that require transfer of electron or protons; using R5-melanin-silica as a bio-inert, UV or radiation absorptive material (e.g. sunscreen additive, cancer treatment, etc.); using silica-coated or CNT-coated magnetic nanoparticles for microwave absorption or electromagnetic interference (EMI) shielding. Specific applications include as coatings on military stealth aircrafts or vehicles and as MRI contrast agents.

DNA nanostructures are currently being explored by others for drug delivery and biosensing. Coating the nanostructures with a bio-inert material, like silica, can improve the efficacy and reduce immune response. Additionally, DNA nanostructures are a robust method for synthesizing highly complex structures at the nanoscale. Coating these structures with silica and removing the organic material can serve as another route to synthesize complex silica structures at the nano- and micro-scales. Using R5 to precipitate silica coatings may enable thinner coatings than alternative chemical methods and may allow for DNA nanostructure morphologies to be retained even after the coatings, thereby allowing the DNA structure to remain functional after being coated with silica. (One common challenge with other methods is the silica completely engulfs the nanostructure.)

Applications for using R5 to synthesize ordered silica spheres on a surface include production of opals for use in jewelry and ornaments.

REFERENCES

1. Adams B. L., Finch A. S., Hurley M. M., Starkes D. A. and Stratis-Cullum D. N., Genetically Engineered Peptides for Inorganics: Study of an Unconstrained Bacterial Display Technology and Bulk Aluminum Alloy, Adv. Mater. 2013 Sep. 6; 25(33): 4530-91.
2. Ahmad G., Dickerson M. B., Cai Y., Jones S. E., Ernst E. M., Vernon J. P., Haluska M. S., Fang Y., Wang J., Subramanyam G., Naik R. R., and Sandhage K. H., Rapid Bioenabled Formation of Ferroelectric BaTiO3 at Room Temperature from an Aqueous Salt Solution at Near Neutral pH. J. Am. Chem. Soc. 2008 Jan. 9; 130(1): 4-5.
3. Amemiya Y., Arakaki A., Staniland S., Tanaka T., and Matsunaga T., Controlled formation of magnetite crystal by partial oxidation of ferrous hydroxide in the presence of recombinant magnetotactic bacterial protein Mms6. Biomaterials, 2007 December; 28(35): 5381-89.
4. Banerjee I. A., Yu L., and Matsui H., Cu nanocrystal growth on peptide nanotubes by biomineralization: Size control of Cu nanocrystals by tuning peptide conformation. Proc. Natl. Acad. Sci. U.S.A. 2003 Dec. 9; 100(25): 14678-82.
5. Bassindale A. R., Codina-Barrios A., Franscione N., and Taylor P. G., An improved phage display methodology for inorganic nanoparticle fabrication. Chem. Commun. 2007 Jul. 28; (28):2956-58.
6. Borg S., Rothenstein D., Bill J., and Schuler D., Generation of Multishell Magnetic Hybrid Nanoparticles by Encapsulation of Genetically Engineered and Fluorescent Bacterial Magnetosomes with ZnO and SiO 2. Small, 2015 Sep. 2; 11(33): 4209-17.
7. Brutchey R. L., Yoo E. S., and Morse D. E., Biocatalytic Synthesis of a Nanostructured and Crystalline Bimetallic Perovskite-like Barium Oxofluorotitanate at Low Temperature. J. Am. Chem. Soc. 2006 Aug. 9; 128(31): 10288-94.
8. Buckley A. M. and Greenblatt, M. J., The sol-gel preparation of silica gels. J. Chem. Educ., 1994 July; 71(7): 599.
9. Castro C. E., Kilchherr F., Kim D. N., Shiao E. L., Wauer T., Wortmann P., Bathe M., and Dietz H., A primer to scaffolded DNA origami. Nat. Methods, 2011 March; 8(3): 221-29.
10. Cha J. N., Shimizu K., Zhou Y., Christiansen S. C., Chmeka B. F., Stucky G. D., and Morse D. E., Silicatein filaments and subunits from a marine sponge direct the polymerization of silica and silicones in vitro. Proc. Natl. Acad. Sci. U.S.A., 1999 Jan. 19; 96(2): 361-65.
11. Chen X., Liu Y., Yang J., Wu W., Miao L., Yu Y., Yang X., and Sun W., The synthesis of hydroxyapatite with different crystallinities by controlling the concentration of recombinant CEMP1 for biological application. Mater. Sci. Eng. C. Mater. Biol. Appl. 2016 February; 59: 384-89.
12. Clark S. and Hammon P., Engineering the Microfabrication of Layer-by-Layer Thin Films. Adv. Mater., 1998 December; 10(18): 1515-19.
13. della-Cioppa G., Garger S. J., Sverlow G. G., Turpen T. H., and Grill L. K., Melanin Production in *Escherichia coli* from a Cloned Tyrosinase Gene. Biotechnology, 1990 July; 8(7): 634-38.
14. Dickerson M. B., Jones S. E., Cai Y., Ahmad G., Naik R. R., Kroger N., and Sandhage K. H., Identification and Design of Peptides for the Rapid, High-Yield Formation of Nanoparticulate TiO2 from Aqueous Solutions at Room Temperature. Chem. Mater. 2008; 20(4): 1578-84.
15. Dickerson M. B., Naik R. R., Stone M. O. Cia Y., and Sandhage K. H., Identification of peptides that promote the rapid precipitation of germania nanoparticle networks via use of a peptide display library. Chem. Commun. 2004 Aug. 7; (15): 1776-77.
16. Ding D., Guerette P. A., Hoon S., Kong K. W., Cornvik T., Nilsson M., Kumar A., Lescar J., and Miserez A., Biomimetic Production of Silk-Like Recombinant Squid Sucker Ring Teeth Proteins. Biomacromolecules. 2014; 15: 3278-89.
17. Djalali R., Chen Y. F., and Matsui H., Au Nanocrystal Growth on Nanotubes Controlled by Conformations and Charges of Sequenced Peptide Templates. J. Am. Chem. Soc. 2003 May 14; 125(19): 5873-79.
18. Filin S. V., Puzynin A. I., and Samoilov V. N., Some Aspects of Precious Opal Synthesis. Australian Gemmologist, 2002 January; 21: 278-282.
19. Flynn C. E., Chuanbin M., Hayhurst A., Williams J. L., Georgiou G., Iverson B., and Belcher A. M., Synthesis and organization of nanoscale II-VI semiconductor materials using evolved peptide specificity and viral capsid assembly. J. Mater. Chem. 2003; 13(10): 2414-21.
20. Golec P., Karczewska-Golec J., Los M., and Wegrzyn G., Novel ZnO-binding peptides obtained by the screening of a phage display peptide library. J. Nanopar. Res. 2012. 14(11): 1218.

21. Guerette P. A., Hoon S., Ding D., Amini S., Masic A., Ravi V., Venkatesh B., Weaver J. C., and Miserez A., Nanoconfined β-Sheets Mechanically Reinforce the Supra-Biomolecular Network of Robust Squid Sucker Ring Teeth. ACS Nano. 2014 Jul. 22; 8(7): 7170-79.
22. Gungormus M., Fong H., Kim I. W., Evans J. S., Tamerler C., and Sarikaya M., Regulation of in vitro Calcium Phosphate Mineralization by Combinatorially Selected Hydroxyapatite-Binding Peptides. Biomacromolecules. 2008 March; 9(3): 966-73.
23. Kang S. H., Bozhilov K. N., Myung N. V., Mulchandani A., and Chen W., Microbial Synthesis of CdS Nanocrystals in Genetically Engineered E. coli. Angew. Chem. Int. Ed. Engl. 2008; 47(28): 5186-89.
24. Kröger N., Deutzmann R., and Sumper M., Polycationic Peptides from Diatom Biosilica That Direct Silica Nanosphere Formation. Science, 1999 Nov. 5; 286(5442): 1129-32.
25. Li C., Botsaris G. D, and Kaplan D. L., Selective in Vitro Effect of Peptides on Calcium Carbonate Crystallization. Cryst. Growth Des. 2002; 2(5): 387-93.
26. Naik R. R., Jones S. E., Murray C. J., McAuliffe J. C., Vaia R. A., and Stone M. O., Peptide Templates for Nanoparticle Synthesis Derived from Polymerase Chain Reaction-Driven Phage Display. Adv. Funct. Mater. 2004; 14(1): 25-30.
27. Naik R. R., Stringer S. J., Agarwal G., Jones S. E., and Stone M. O., Biomimetic synthesis and patterning of silver nanoparticles. Nat. Mater. 2002 November; 1(3): 169-72.
28. Nam K. T., Kim D. W., Yoo P. J., Chiang C. Y., Meethong N., Hammond P. T. Chiang Y. M., and Blecher A. M., Virus-Enabled Synthesis and Assembly of Nanowires for Lithium Ion Battery Electrodes. Science. 2006 May 12; 312(5775): 885-88.
29. Okochi M., Ogawa M., Kaga C., Sugita T., Tomita Y., Kato R., and Honda H., Screening of peptide with a high affinity for ZnO using spot-synthesized peptide arrays and computational analysis. Acta. Biomater. 2010 June; 6(6): 2301-06.
30. Pappalardo G., Giuseppe I., Raffaele P. B., Tiziana C., Giulia G. and Saita M. G., Copper(ii) and nickel(ii) binding modes in a histidine-containing model dodecapeptide. New J. Chem. 2002; 26(5): 593-600.
31. Prince J. T., McGrath K. P., DiGirolamo C. M., and Kaplan D. L., Construction, Cloning, and Expression of Synthetic Genes Encoding Spider Dragline Silk. Biochemistry. 1995 Aug. 29; 34: 10879-85.
32. Roy M. D., Scott K. S., Amis E. J., and Becker M. L., Identification of a Highly Specific Hydroxyapatite-binding Peptide using Phage Display. Adv. Mater. 2008; 20(10): 1830-36.
33. Sumerel J. L., Yang W., Kisailus D., Weaver J. C., Choi J. H., and Morse D. E., Biocatalytically Templated Synthesis of Titanium Dioxide. Chem. Mater. 2003; 15(25): 4804-9.
34. Schweitzer A. D., Revskaya E., Chu P., Pazo V., Friedman M., Nosanchuk J. D., Cahill S., Frases S., Casadevall A., and Dadachova E., Melanin-covered nanoparticles for protection of bone marrow during radiation therapy of cancer. Int. J. Radiat. Oncol. Biol. Phys., 2010 Dec. 1; 78(5): 1494-1502.
35. Thai C. K., Dai H., Sastry M. S., Sarikaya M., Schwartz D. T., and Baneyz F., Identification and characterization of Cu2O- and ZnO-binding polypeptides by Escherichia coli cell surface display: toward an understanding of metal oxide binding. Biotechnol. Bioengin. 2004 Jul. 20; 87(2): 129-37.
36. Tsiveriotis P. and Hadjiliadis N., Studies on the interaction of histidyl containing peptides with palladium(II) and platinum(II) complex ions. Coord. Chem. Rev. 1999; 171-84.
37. Umetsu M., Mizuta M., Tsumoto K., Ohara S., Takami S., Watanabe H., Kumagai I., and Adschiri T., Bioassisted Room-Temperature Immobilization and Mineralization of Zinc Oxide The Structural Ordering of ZnO Nanoparticles into a Flower-Type Morphology. Adv. Mater. 2005; 17(21): 2571-75.
38. Zafar M. S., Belton D. J., Hanby B., Kaplan D. L., and Perry C. C., Functional Material Feature of *Bombyx mori* Silk Light vs. Heavy Chain Proteins. Biomacromolecules. 2015; 16(2): 606-14.
39. Zhang Y., Aheng F., Yang T., Zhou W., Liu Y., Man N., Zhang L., Jin N., Dou Q., Zhang Y., Li Z., and Wen L. P., Tuning the autophagy-inducing activity of lanthanide-based nanocrystals through specific surface-coating peptides. Nat. Mater. 2012 September; 11(9):817-26.
40. Zuo R., D. Ornek, and T. K. Wood, Aluminum- and mild steel-binding peptides from phage display. Appl. Microbiol. Biotechnol. 2005 September; 68(4): 505-9.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

"Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

What is claimed is:

1. A synthetic molecule comprising or consisting essentially of the amino acid sequence of SEQ ID NO: 1, wherein at least one amino acid of SEQ ID NO: 1 contains a non-native post-translational modification selected from the group consisting of oxidation, myristoylation, hypusination, and methylation, wherein the methylation occurs at Lys3, Lys4, and/or Lys15 of SEQ ID NO: 1.

2. The synthetic molecule of claim 1, wherein the oxidation occurs at Tyr10 of SEQ ID NO: 1.

3. A polymer comprising a fusion of at least two synthetic molecules of claim 1.

4. The polymer of claim 3, wherein two or more of the synthetic molecules contain an oxidized tyrosine.

5. A silica structure comprising precipitated silica and at least one polymer as claimed in claim 3.

6. The polymer of claim 3, wherein:
two or more of the at least two synthetic molecules are chemically unique;
the at least two synthetic molecules are fused through an interaction between at least one terminal end of each synthetic molecule; and/or
the at least two synthetic molecules are fused through an interaction between at least one amino acid side chain of each synthetic molecule.

7. A composition comprising at least one synthetic molecule as claimed in claim 1 and/or at least one polymer thereof.

8. A method of synthesizing a silica structure comprising: contacting a synthetic molecule as claimed in claim 1 with a solution comprising dissolved silica.

9. The method of claim 8, wherein:
the synthetic molecule and the solution comprising dissolved silica are contacted at ambient temperature;
the dissolved silica is aqueous silicic acid or colloidal silica;
the synthetic molecule and the solution comprising dissolved silica are further contacted with at least one metal nanoparticle, optionally wherein the at least one metal nanoparticle is selected from the group consisting of an iron oxide nanoparticle, a zinc oxide nanoparticle, tantalum oxide nanoparticles, a hafnium oxide nanoparticle, a titanium oxide nanoparticle, a cadmium sulfide nanoparticle, a germanium oxide nanoparticle, an indium phosphide, and a cadmium selenide nanoparticle;
the synthetic molecule and the solution comprising dissolved silica are further contacted with magnetosomes; and/or
the synthetic molecule and the solution comprising dissolved silica are further contacted with a biomolecule, optionally wherein the biomolecule is DNA.

10. A silica structure comprising precipitated silica and at least one synthetic molecule as claimed in claim 1.

11. The silica structure of claim 10, further comprising:
iron oxide nanoparticles;
magnetosomes, optionally wherein at least one of the at least one synthetic molecules is R5-MamC, R5-CNT1, or R5-CNT2; and/or
a biomolecule, optionally wherein the biomolecule is DNA.

12. The synthetic molecule of claim 1, wherein Lys3, Lys4, and/or Lys15 of SEQ ID NO: 1 is methylated more than once.

13. The synthetic molecule of claim 1, wherein at least one amino acid of SEQ ID NO: 1 further contains a post-translational modification selected from the group consisting of:
phosphorylation, optionally wherein the phosphorylation occurs at Ser1, Ser2, Ser5, Ser7, Ser9, Ser11, and/or Ser14 of SEQ ID NO: 1;
methylation, wherein the methylation occurs at Lys 12 of SEQ ID NO:1, and optionally wherein Lys12 of SEQ ID NO: 1 is methylated more than once; and
propylamination, optionally wherein the propylamination is the addition of spermine, spermidine, putrescine, and/or thermospermine to at least one amino acid of SEQ ID NO: 1.

14. A synthetic molecule comprising: a silica binding protein comprising the amino acid sequence of SEQ ID NO: 1, wherein at least one amino acid of SEQ ID NO: 1 contains a non-native post-translational modification selected from the group consisting of oxidation, myristoylation, hypusination, and methylation, wherein the methylation occurs at Lys3, Lys4, and/or Lys15 of SEQ ID NO: 1; and a terminal fusion molecule, wherein the terminal fusion molecule is:
(i) a metal-binding polypeptide, a magnetosome surface polypeptide, or a carbon-nanotube-binding polypeptide; and
(ii) fused to at least one terminal end of the silica-binding peptide.

15. The synthetic molecule of claim 14, wherein the synthetic molecule comprises an additional terminal fusion molecule, wherein the additional terminal fusion molecule is not a biomolecule.

16. The synthetic molecule of claim 14, wherein at least one amino acid of the silica binding peptide contains a post-translational modification selected from the group consisting of propylamination, hydroxylation, adenylylation, biotinylation, lipidation, acetylation, glycosylation, propylamination, and sulfonation.

17. The synthetic molecule of claim 14, wherein the oxidation occurs at Tyr10 of SEQ ID NO:1.

18. The synthetic molecule of claim 14, wherein the terminal fusion molecule is a polypeptide selected from the group consisting of Mms6, MamC, CNT1, and CNT2.

19. The synthetic molecule of claim 14, wherein Lys3, Lys4, and/or Lys15 of SEQ ID NO: 1 is methylated more than once.

20. The synthetic molecule of claim 14, wherein at least one amino acid of SEQ ID NO: 1 contains a post-translational modification selected from the group consisting of:
- phosphorylation, optionally wherein the phosphorylation occurs at Ser1, Ser2, Ser5, Ser7, Ser9, Ser11, and/or Ser14 of SEQ ID NO: 1;
- methylation, wherein the methylation occurs at Lys 12 of SEQ ID NO:1, and optionally, wherein Lys12 of SEQ ID NO: 1 is methylated more than once; and
- propylamination, optionally wherein the propylamination is the addition of spermine, spermidine, putrescine, and/or thermospermine to at least one amino acid of SEQ ID NO: 1.

\* \* \* \* \*

SEQUENCE LISTING

```
<160> NUMBER OF SEQ ID NOS: 94

<210> SEQ ID NO 1
<211> LENGTH: 19
<212> TYPE: PRT
<213> ORGANISM: Artificial Sequence
<220> FEATURE:
<223> OTHER INFORMATION: Silica-Binding Peptide

<400> SEQUENCE: 1

Ser Ser Lys Lys Ser Gly Ser Tyr Ser Gly Ser Lys Gly Ser Lys Arg
1               5                   10                  15

Arg Ile Leu
```

<210> SEQ ID NO 2
<211> LENGTH: 33
<212> TYPE: PRT
<213> ORGANISM: Artificial Sequence
<220> FEATURE:
<223> OTHER INFORMATION: Silica-Binding Peptide

<400> SEQUENCE: 2

Ser Ser Lys Lys Ser Gly Ser Tyr Tyr Ser Tyr Gly Thr Lys Lys Ser
1               5                   10                  15

Gly Ser Tyr Ser Gly Tyr Ser Thr Lys Lys Ser Ala Ser Arg Arg Ile
            20                  25                  30

Leu

<210> SEQ ID NO 3
<211> LENGTH: 12
<212> TYPE: PRT
<213> ORGANISM: Artificial Sequence
<220> FEATURE:
<223> OTHER INFORMATION: Silica-Binding Peptide

<400> SEQUENCE: 3

Ala Pro Pro Gly His His His Trp His Ile His His
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Silica-Binding Peptide

<400> SEQUENCE: 4

Met Ser Ala Ser Ser Tyr Ala Ser Phe Ser Trp Ser
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Silica-Binding Peptide

<400> SEQUENCE: 5

Lys Pro Ser His His His His His Thr Gly Ala Asn
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Silica-Binding Peptide

<400> SEQUENCE: 6

Met Ser Pro His Pro His Pro Arg His His His Thr
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Silica-Binding Peptide

<400> SEQUENCE: 7

```
Met Ser Pro His His Met His His Ser His Gly His
1               5                   10
```

<210> SEQ ID NO 8
<211> LENGTH: 12
<212> TYPE: PRT
<213> ORGANISM: Artificial Sequence
<220> FEATURE:
<223> OTHER INFORMATION: Silica-Binding Peptide

<400> SEQUENCE: 8

```
Leu Pro His His His His Leu His Thr Lys Leu Pro
1               5                   10
```

<210> SEQ ID NO 9
<211> LENGTH: 12
<212> TYPE: PRT
<213> ORGANISM: Artificial Sequence
<220> FEATURE:
<223> OTHER INFORMATION: Silica-Binding Peptide

<400> SEQUENCE: 9

```
Ala Pro His His His His Pro His His Leu Ser Arg
1               5                   10
```

<210> SEQ ID NO 10
<211> LENGTH: 12
<212> TYPE: PRT
<213> ORGANISM: Artificial Sequence
<220> FEATURE:
<223> OTHER INFORMATION: Silica-Binding Peptide

<400> SEQUENCE: 10

```
Arg Gly Arg Arg Arg Arg Leu Ser Cys Arg Leu Leu
1               5                   10
```

<210> SEQ ID NO 11
<211> LENGTH: 12
<212> TYPE: PRT
<213> ORGANISM: Artificial Sequence
<220> FEATURE:
<223> OTHER INFORMATION: Silica-Binding Peptide

<400> SEQUENCE: 11

```
Thr Val Ala Ser Asn Ser Gly Leu Arg Pro Ala Ser
1               5                   10
```

<210> SEQ ID NO 12
<211> LENGTH: 20
<212> TYPE: PRT
<213> ORGANISM: Artificial Sequence
<220> FEATURE:
<223> OTHER INFORMATION: Silica-Binding Peptide

<400> SEQUENCE: 12

```
Ser Ser Lys Lys Ser Gly Ser Tyr Ser Gly Ser Lys Gly Ser Lys Arg
1               5                   10                  15

Arg Ile Asn Leu
            20
```

<210> SEQ ID NO 13
<211> LENGTH: 19
<212> TYPE: PRT
<213> ORGANISM: Artificial Sequence
<220> FEATURE:
<223> OTHER INFORMATION: Silica-Binding Peptide

<400> SEQUENCE: 13

Ser Ser Lys Lys Ser Gly Ser Tyr Ser Gly Lys Gly Ser Lys Arg
1               5                   10                  15

Arg Asn Leu

<210> SEQ ID NO 14
<211> LENGTH: 17
<212> TYPE: PRT
<213> ORGANISM: Artificial Sequence
<220> FEATURE:
<223> OTHER INFORMATION: Silica-Binding Peptide

<400> SEQUENCE: 14

Gly Met Ser Ser Lys Lys Ser Gly Ser Lys Gly Ser Lys Arg Arg Ile
1               5                   10                  15

Leu

<210> SEQ ID NO 15
<211> LENGTH: 19
<212> TYPE: PRT
<213> ORGANISM: Artificial Sequence
<220> FEATURE:
<223> OTHER INFORMATION: Silica-Binding Peptide

<400> SEQUENCE: 15

Ser Ser Glu Glu Ser Gly Ser Tyr Ser Gly Ser Glu Gly Ser Lys Arg
1               5                   10                  15

Arg Ile Leu

<210> SEQ ID NO 16
<211> LENGTH: 19
<212> TYPE: PRT
<213> ORGANISM: Artificial Sequence
<220> FEATURE:
<223> OTHER INFORMATION: Silica-Binding Peptide

<400> SEQUENCE: 16

Ser Ser Asp Asp Ser Gly Ser Tyr Ser Gly Ser Asp Gly Ser Lys Arg
1               5                   10                  15

Arg Ile Leu

<210> SEQ ID NO 17
<211> LENGTH: 19
<212> TYPE: PRT
<213> ORGANISM: Artificial Sequence
<220> FEATURE:
<223> OTHER INFORMATION: Silica-Binding Peptide

<400> SEQUENCE: 17

Ser Ser Lys Glu Ser Gly Ser Tyr Ser Gly Ser Glu Gly Ser Lys Arg
1               5                   10                  15

Arg Ile Leu

<210> SEQ ID NO 18
<211> LENGTH: 19
<212> TYPE: PRT
<213> ORGANISM: Artificial Sequence
<220> FEATURE:
<223> OTHER INFORMATION: Silica-Binding Peptide

<400> SEQUENCE: 18

Ser Ser Lys Lys Ser Gly Ser Tyr Ser Gly Ser Glu Gly Ser Lys Arg

```
1               5                   10                  15

Arg Ile Leu

<210> SEQ ID NO 19
<211> LENGTH: 19
<212> TYPE: PRT
<213> ORGANISM: Artificial Sequence
<220> FEATURE:
<223> OTHER INFORMATION: Silica-Binding Peptide

<400> SEQUENCE: 19

Ser Ser Lys Glu Ser Gly Ser Tyr Ser Gly Ser Lys Gly Ser Lys Arg
1               5                   10                  15

Arg Ile Leu

<210> SEQ ID NO 20
<211> LENGTH: 19
<212> TYPE: PRT
<213> ORGANISM: Artificial Sequence
<220> FEATURE:
<223> OTHER INFORMATION: Silica-Binding Peptide

<400> SEQUENCE: 20

Ser Ser Lys Lys Ser Gly Ser Leu Ser Gly Ser Lys Gly Ser Lys Arg
1               5                   10                  15

Arg Ile Leu

<210> SEQ ID NO 21
<211> LENGTH: 19
<212> TYPE: PRT
<213> ORGANISM: Artificial Sequence
<220> FEATURE:
<223> OTHER INFORMATION: Silica-Binding Peptide

<400> SEQUENCE: 21

Cys Cys Lys Lys Cys Gly Cys Tyr Cys Gly Cys Lys Gly Cys Lys Arg
1               5                   10                  15

Arg Ile Leu

<210> SEQ ID NO 22
<211> LENGTH: 19
<212> TYPE: PRT
<213> ORGANISM: Artificial Sequence
<220> FEATURE:
<223> OTHER INFORMATION: Silica-Binding Peptide

<400> SEQUENCE: 22

Ala Ala Lys Lys Ala Gly Ala Tyr Ala Gly Ala Lys Gly Ala Lys Arg
1               5                   10                  15

Arg Ile Leu

<210> SEQ ID NO 23
<211> LENGTH: 19
<212> TYPE: PRT
<213> ORGANISM: Artificial Sequence
<220> FEATURE:
<223> OTHER INFORMATION: Silica-Binding Peptide

<400> SEQUENCE: 23

Ser Ser Lys Lys Ala Gly Ala Tyr Ala Gly Ala Lys Gly Ala Lys Arg
1               5                   10                  15

Arg Ile Leu
```

```
<210> SEQ ID NO 24
<211> LENGTH: 19
<212> TYPE: PRT
<213> ORGANISM: Artificial Sequence
<220> FEATURE:
<223> OTHER INFORMATION: Silica-Binding Peptide

<400> SEQUENCE: 24

Ile Ile Lys Lys Ile Gly Ile Ile Gly Ile Lys Gly Ile Lys Arg
1               5                   10                  15

Arg Ile Leu

<210> SEQ ID NO 25
<211> LENGTH: 19
<212> TYPE: PRT
<213> ORGANISM: Artificial Sequence
<220> FEATURE:
<223> OTHER INFORMATION: Silica-Binding Peptide

<400> SEQUENCE: 25

Pro Pro Lys Lys Pro Gly Pro Pro Gly Pro Lys Gly Pro Lys Arg
1               5                   10                  15

Arg Ile Leu

<210> SEQ ID NO 26
<211> LENGTH: 19
<212> TYPE: PRT
<213> ORGANISM: Artificial Sequence
<220> FEATURE:
<223> OTHER INFORMATION: Silica-Binding Peptide

<400> SEQUENCE: 26

Asp Asp Lys Lys Asp Gly Asp Tyr Asp Gly Asp Lys Gly Asp Lys Arg
1               5                   10                  15

Arg Ile Leu

<210> SEQ ID NO 27
<211> LENGTH: 19
<212> TYPE: PRT
<213> ORGANISM: Artificial Sequence
<220> FEATURE:
<223> OTHER INFORMATION: Silica-Binding Peptide

<400> SEQUENCE: 27

Asn Asn Glu Glu Asn Gly Asn Tyr Asn Gly Asn Glu Gly Asn Lys Arg
1               5                   10                  15

Arg Ile Leu

<210> SEQ ID NO 28
<211> LENGTH: 19
<212> TYPE: PRT
<213> ORGANISM: Artificial Sequence
<220> FEATURE:
<223> OTHER INFORMATION: Silica-Binding Peptide

<400> SEQUENCE: 28

Asn Asn Glu Lys Asn Gly Asn Tyr Asn Gly Asn Glu Gly Asn Lys Arg
1               5                   10                  15

Arg Ile Leu

<210> SEQ ID NO 29
<211> LENGTH: 19
<212> TYPE: PRT
```

```
<213> ORGANISM: Artificial Sequence
<220> FEATURE:
<223> OTHER INFORMATION: Silica-Binding Peptide

<400> SEQUENCE: 29

His His Lys Lys His Gly His Tyr His Gly His Lys Gly His Lys Arg
1               5                   10                  15

Arg Ile Leu

<210> SEQ ID NO 30
<211> LENGTH: 19
<212> TYPE: PRT
<213> ORGANISM: Artificial Sequence
<220> FEATURE:
<223> OTHER INFORMATION: Silica-Binding Peptide

<400> SEQUENCE: 30

Lys Lys Lys Lys Lys Gly Lys Tyr Lys Gly Lys Lys Gly Lys Lys Arg
1               5                   10                  15

Arg Ile Leu

<210> SEQ ID NO 31
<211> LENGTH: 19
<212> TYPE: PRT
<213> ORGANISM: Artificial Sequence
<220> FEATURE:
<223> OTHER INFORMATION: Silica-Bindingn Peptide

<400> SEQUENCE: 31

Glu Glu Lys Lys Glu Gly Glu Tyr Glu Gly Glu Lys Gly Glu Lys Arg
1               5                   10                  15

Arg Ile Leu

<210> SEQ ID NO 32
<211> LENGTH: 19
<212> TYPE: PRT
<213> ORGANISM: Artificial Sequence
<220> FEATURE:
<223> OTHER INFORMATION: Silica-Binding Peptide

<400> SEQUENCE: 32

Ala Ala Glu Glu Ala Gly Ala Tyr Ala Gly Ala Glu Gly Ala Lys Arg
1               5                   10                  15

Arg Ile Leu

<210> SEQ ID NO 33
<211> LENGTH: 19
<212> TYPE: PRT
<213> ORGANISM: Artificial Sequence
<220> FEATURE:
<223> OTHER INFORMATION: Silica-Binding Peptide

<400> SEQUENCE: 33

Ala Ala Glu Lys Ala Gly Ala Tyr Ala Gly Ala Glu Gly Ala Lys Arg
1               5                   10                  15

Arg Ile Leu

<210> SEQ ID NO 34
<211> LENGTH: 19
<212> TYPE: PRT
<213> ORGANISM: Artificial Sequence
<220> FEATURE:
<223> OTHER INFORMATION: Silica-Binding Peptide
```

```
<400> SEQUENCE: 34

Ser Ser His His Ser Gly Ser Tyr Ser Gly Ser His Gly Ser Lys Arg
1               5                   10                  15

Arg Ile Leu

<210> SEQ ID NO 35
<211> LENGTH: 15
<212> TYPE: PRT
<213> ORGANISM: Artificial Sequence
<220> FEATURE:
<223> OTHER INFORMATION: DBAD1

<400> SEQUENCE: 35

Ser Thr Glu Ala Arg Ala Thr Thr Leu Thr Ala Cys Asp Ala Tyr
1               5                   10                  15

<210> SEQ ID NO 36
<211> LENGTH: 12
<212> TYPE: PRT
<213> ORGANISM: Artificial Sequence
<220> FEATURE:
<223> OTHER INFORMATION: A1-S1

<400> SEQUENCE: 36

Val Pro Ser Ser Gly Pro Gln Asp Thr Arg Thr Thr
1               5                   10

<210> SEQ ID NO 37
<211> LENGTH: 12
<212> TYPE: PRT
<213> ORGANISM: Artificial Sequence
<220> FEATURE:
<223> OTHER INFORMATION: A1-S2

<400> SEQUENCE: 37

Tyr Ser Pro Asp Pro Arg Pro Trp Ser Ser Asp Tyr
1               5                   10

<210> SEQ ID NO 38
<211> LENGTH: 12
<212> TYPE: PRT
<213> ORGANISM: Artificial Sequence
<220> FEATURE:
<223> OTHER INFORMATION: BT1

<400> SEQUENCE: 38

His Gln Pro Ala Asn Asp Pro Ser Trp Tyr Thr Gly
1               5                   10

<210> SEQ ID NO 39
<211> LENGTH: 12
<212> TYPE: PRT
<213> ORGANISM: Artificial Sequence
<220> FEATURE:
<223> OTHER INFORMATION: BT2

<400> SEQUENCE: 39

Asn Thr Ile Ser Gly Leu Arg Tyr Ala Pro His Met
1               5                   10

<210> SEQ ID NO 40
<211> LENGTH: 9
<212> TYPE: PRT
<213> ORGANISM: Artificial Sequence
<220> FEATURE:
<223> OTHER INFORMATION: A7
```

```
<400> SEQUENCE: 40

Cys Asn Asn Pro Met His Gln Asn Cys
1               5

<210> SEQ ID NO 41
<211> LENGTH: 12
<212> TYPE: PRT
<213> ORGANISM: Artificial Sequence
<220> FEATURE:
<223> OTHER INFORMATION: Z8

<400> SEQUENCE: 41

Leu Arg Arg Ser Ser Glu Ala His Asn Ser Ile Val
1               5                   10

<210> SEQ ID NO 42
<211> LENGTH: 9
<212> TYPE: PRT
<213> ORGANISM: Artificial Sequence
<220> FEATURE:
<223> OTHER INFORMATION: J182

<400> SEQUENCE: 42

Cys Thr Tyr Ser Arg Leu His Leu Cys
1               5

<210> SEQ ID NO 43
<211> LENGTH: 12
<212> TYPE: PRT
<213> ORGANISM: Artificial Sequence
<220> FEATURE:
<223> OTHER INFORMATION: J140

<400> SEQUENCE: 43

Ser Leu Thr Pro Leu Thr Thr Ser His Leu Arg Ser
1               5                   10

<210> SEQ ID NO 44
<211> LENGTH: 15
<212> TYPE: PRT
<213> ORGANISM: Artificial Sequence
<220> FEATURE:
<223> OTHER INFORMATION: 5R39

<400> SEQUENCE: 44

Gly Arg Val Leu Ala Gly Ser Ser Ala Val Ser Ser Arg Pro Ser
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: 4R12

<400> SEQUENCE: 45

Ala Tyr Gly Ser Ser Gly Phe Tyr Ser Ala Ser Phe Thr Pro Arg
1               5                   10                  15

<210> SEQ ID NO 46
<211> LENGTH: 12
<212> TYPE: PRT
<213> ORGANISM: Artificial Sequence
<220> FEATURE:
<223> OTHER INFORMATION: AG-4
```

```
<400> SEQUENCE: 46

Asn Pro Ser Ser Leu Phe Arg Tyr Leu Pro Ser Asp
1               5                   10

<210> SEQ ID NO 47
<211> LENGTH: 11
<212> TYPE: PRT
<213> ORGANISM: Artificial Sequence
<220> FEATURE:
<223> OTHER INFORMATION: AG-P35

<400> SEQUENCE: 47

Trp Ser Trp Arg Pro Thr Pro His Val Val Thr
1               5                   10

<210> SEQ ID NO 48
<211> LENGTH: 11
<212> TYPE: PRT
<213> ORGANISM: Artificial Sequence
<220> FEATURE:
<223> OTHER INFORMATION: Co1-P10

<400> SEQUENCE: 48

His Tyr Pro Thr Leu Pro Gly Ser Ser Thr Thr
1               5                   10

<210> SEQ ID NO 49
<211> LENGTH: 12
<212> TYPE: PRT
<213> ORGANISM: Artificial Sequence
<220> FEATURE:
<223> OTHER INFORMATION: CN225

<400> SEQUENCE: 49

Arg His Thr Asp Gly Leu Arg Arg Ile Ala Ala Arg
1               5                   10

<210> SEQ ID NO 50
<211> LENGTH: 12
<212> TYPE: PRT
<213> ORGANISM: Artificial Sequence
<220> FEATURE:
<223> OTHER INFORMATION: CN44

<400> SEQUENCE: 50

Asn Thr Val Trp Arg Leu Asn Ser Ser Cys Gly Met
1               5                   10

<210> SEQ ID NO 51
<211> LENGTH: 12
<212> TYPE: PRT
<213> ORGANISM: Artificial Sequence
<220> FEATURE:
<223> OTHER INFORMATION: CN179

<400> SEQUENCE: 51

Arg Ile Gly His Gly Arg Gln Ile Arg Lys Pro Leu
1               5                   10

<210> SEQ ID NO 52
<211> LENGTH: 12
<212> TYPE: PRT
<213> ORGANISM: Artificial Sequence
<220> FEATURE:
<223> OTHER INFORMATION: CN146

<400> SEQUENCE: 52
```

```
Met Arg His Ser Ser Gly Glu Pro Arg Leu Leu
1               5                   10

<210> SEQ ID NO 53
<211> LENGTH: 12
<212> TYPE: PRT
<213> ORGANISM: Artificial Sequence
<220> FEATURE:
<223> OTHER INFORMATION: HG12

<400> SEQUENCE: 53

His Gly Gly Gly His Gly His Gly Gly Gly His Gly
1               5                   10

<210> SEQ ID NO 54
<211> LENGTH: 6
<212> TYPE: PRT
<213> ORGANISM: Artificial Sequence
<220> FEATURE:
<223> OTHER INFORMATION: HG6

<400> SEQUENCE: 54

His Gly Gly Gly His Gly
1               5

<210> SEQ ID NO 55
<211> LENGTH: 12
<212> TYPE: PRT
<213> ORGANISM: Artificial Sequence
<220> FEATURE:
<223> OTHER INFORMATION: Ge8

<400> SEQUENCE: 55

Ser Leu Lys Met Pro His Trp Pro His Leu Leu Pro
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Ge34

<400> SEQUENCE: 56

Thr Gly His Gln Ser Pro Gly Ala Tyr Ala Ala His
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Gold-binding peptide

<400> SEQUENCE: 57

Leu Lys Ala His Leu Pro Pro Ser Arg Leu Pro Ser
1               5                   10

<210> SEQ ID NO 58
<211> LENGTH: 8
<212> TYPE: PRT
<213> ORGANISM: Artificial Sequence
<220> FEATURE:
<223> OTHER INFORMATION: Gold-binding peptide

<400> SEQUENCE: 58
```

Ala His His Ala His Ala Ala Asp
1               5

<210> SEQ ID NO 59
<211> LENGTH: 12
<212> TYPE: PRT
<213> ORGANISM: Artificial Sequence
<220> FEATURE:
<223> OTHER INFORMATION: MS-S1

<400> SEQUENCE: 59

Ala Thr Ile His Asp Ala Phe Tyr Ser Ala Pro Glu
1               5                   10

<210> SEQ ID NO 60
<211> LENGTH: 11
<212> TYPE: PRT
<213> ORGANISM: Artificial Sequence
<220> FEATURE:
<223> OTHER INFORMATION: RE-1

<400> SEQUENCE: 60

Ala Cys Thr Ala Arg Ser Pro Trp Ile Cys Gly
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Ag-22

<400> SEQUENCE: 61

Thr Val Pro Pro Lys Ala Pro Arg Ser Ser Asp Leu
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Ag-28

<400> SEQUENCE: 62

Leu Thr Arg Pro Asn His Gly Asn Thr Val Asp Thr
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Pt-41

<400> SEQUENCE: 63

Ser Arg Leu Thr His Ser Asn Tyr Ala Thr Pro Thr
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Pt-14

<400> SEQUENCE: 64

Glu His Thr Asn Pro Ile Leu Ser His Thr His Asn

```
1               5              10
```

<210> SEQ ID NO 65
<211> LENGTH: 12
<212> TYPE: PRT
<213> ORGANISM: Artificial Sequence
<220> FEATURE:
<223> OTHER INFORMATION: Pt-1.2

<400> SEQUENCE: 65

```
Gln Ser Phe Ser Thr Asn Val Leu His Thr His His
1               5                   10
```

<210> SEQ ID NO 66
<211> LENGTH: 5
<212> TYPE: PRT
<213> ORGANISM: Artificial Sequence
<220> FEATURE:
<223> OTHER INFORMATION: HPGAH

<400> SEQUENCE: 66

```
His Pro Gly Ala His
1               5
```

<210> SEQ ID NO 67
<211> LENGTH: 12
<212> TYPE: PRT
<213> ORGANISM: Artificial Sequence
<220> FEATURE:
<223> OTHER INFORMATION: AG3

<400> SEQUENCE: 67

```
Ala Tyr Ser Ser Gly Ala Pro Pro Met Pro Pro Phe
1               5                   10
```

<210> SEQ ID NO 68
<211> LENGTH: 12
<212> TYPE: PRT
<213> ORGANISM: Artificial Sequence
<220> FEATURE:
<223> OTHER INFORMATION: AG4

<400> SEQUENCE: 68

```
Asn Pro Ser Ser Leu Phe Arg Tyr Leu Pro Ser Asp
1               5                   10
```

<210> SEQ ID NO 69
<211> LENGTH: 16
<212> TYPE: PRT
<213> ORGANISM: Artificial Sequence
<220> FEATURE:
<223> OTHER INFORMATION: dTi-1(RKK)

<400> SEQUENCE: 69

```
Arg Lys Lys Arg Lys Lys Arg Lys Arg Lys Lys Gly Gly Gly Trp
1               5                   10                  15
```

<210> SEQ ID NO 70
<211> LENGTH: 16
<212> TYPE: PRT
<213> ORGANISM: Artificial Sequence
<220> FEATURE:
<223> OTHER INFORMATION: Ti-1

<400> SEQUENCE: 70

```
Arg Lys Lys Arg Thr Lys Asn Pro Thr His Lys Leu Phe Phe Phe Trp
1               5                   10                  15
```

```
<210> SEQ ID NO 71
<211> LENGTH: 12
<212> TYPE: PRT
<213> ORGANISM: Artificial Sequence
<220> FEATURE:
<223> OTHER INFORMATION: PG-7

<400> SEQUENCE: 71

Thr Met Gly Ala Asn Leu Gly Leu Lys Trp Pro Val
1               5                   10

<210> SEQ ID NO 72
<211> LENGTH: 12
<212> TYPE: PRT
<213> ORGANISM: Artificial Sequence
<220> FEATURE:
<223> OTHER INFORMATION: ZnO-1

<400> SEQUENCE: 72

Glu Ala His Val Met His Lys Val Ala Pro Arg Pro
1               5                   10

<210> SEQ ID NO 73
<211> LENGTH: 6
<212> TYPE: PRT
<213> ORGANISM: Artificial Sequence
<220> FEATURE:
<223> OTHER INFORMATION: ZnO-1

<400> SEQUENCE: 73

His Val Asn Leu His Ser
1               5

<210> SEQ ID NO 74
<211> LENGTH: 6
<212> TYPE: PRT
<213> ORGANISM: Artificial Sequence
<220> FEATURE:
<223> OTHER INFORMATION: ZnO-2

<400> SEQUENCE: 74

Arg Cys Ala Arg Arg Tyr
1               5

<210> SEQ ID NO 75
<211> LENGTH: 6
<212> TYPE: PRT
<213> ORGANISM: Artificial Sequence
<220> FEATURE:
<223> OTHER INFORMATION: ZnO-3

<400> SEQUENCE: 75

His Tyr Gln Ser Asn Trp
1               5

<210> SEQ ID NO 76
<211> LENGTH: 6
<212> TYPE: PRT
<213> ORGANISM: Artificial Sequence
<220> FEATURE:
<223> OTHER INFORMATION: ZnO-4

<400> SEQUENCE: 76

His Trp Phe His Pro Arg
1               5
```

<210> SEQ ID NO 77
<211> LENGTH: 12
<212> TYPE: PRT
<213> ORGANISM: Artificial Sequence
<220> FEATURE:
<223> OTHER INFORMATION: HA 6-1

<400> SEQUENCE: 77

Ser Val Ser Val Gly Met Lys Pro Ser Pro Arg Pro
1               5                   10

<210> SEQ ID NO 78
<211> LENGTH: 9
<212> TYPE: PRT
<213> ORGANISM: Artificial Sequence
<220> FEATURE:
<223> OTHER INFORMATION: HABP1

<400> SEQUENCE: 78

Cys Met Leu Pro His His Gly Ala Cys
1               5

<210> SEQ ID NO 79
<211> LENGTH: 9
<212> TYPE: PRT
<213> ORGANISM: Artificial Sequence
<220> FEATURE:
<223> OTHER INFORMATION: HABP2

<400> SEQUENCE: 79

Cys Asn Pro Gly Phe Ala Gln Ala Cys
1               5

<210> SEQ ID NO 80
<211> LENGTH: 35
<212> TYPE: PRT
<213> ORGANISM: Artificial Sequence
<220> FEATURE:
<223> OTHER INFORMATION: MaSp1 Monomer

<400> SEQUENCE: 80

Ser Gly Arg Gly Gly Leu Gly Gly Gln Gly Ala Gly Met Ala Ala Ala
1               5                   10                  15

Ala Ala Met Gly Gly Ala Gly Gln Gly Gly Tyr Gly Gly Leu Gly Ser
            20                  25                  30

Gln Gly Thr
        35

<210> SEQ ID NO 81
<211> LENGTH: 59
<212> TYPE: PRT
<213> ORGANISM: Artificial Sequence
<220> FEATURE:
<223> OTHER INFORMATION: Fibroin Heavy Monomer

<400> SEQUENCE: 81

Gly Ala Gly Ala Gly Ser Gly Ala Ala Gly Ser Gly Ala Gly Ala Gly
1               5                   10                  15

Ser Gly Ala Gly Ala Gly Ser Gly Ala Gly Ala Gly Ser Gly Ala Gly
            20                  25                  30

Ala Gly Ser Gly Ala Gly Ala Gly Ser Gly Ala Gly Ala Gly Ser Gly
        35                  40                  45

Ala Gly Ala Gly Ser Gly Ala Gly Ala Gly Tyr
    50                  55

```
<210> SEQ ID NO 82
<211> LENGTH: 10
<212> TYPE: PRT
<213> ORGANISM: Artificial Sequence
<220> FEATURE:
<223> OTHER INFORMATION: M1 Region

<400> SEQUENCE: 82

Ala Ala Thr Ser Val Ser Arg Thr Thr His
1               5                   10

<210> SEQ ID NO 83
<211> LENGTH: 12
<212> TYPE: PRT
<213> ORGANISM: Artificial Sequence
<220> FEATURE:
<223> OTHER INFORMATION: M1 Region

<400> SEQUENCE: 83

Ala Thr Thr Ala Val Ser His Thr Thr His His Ala
1               5                   10

<210> SEQ ID NO 84
<211> LENGTH: 11
<212> TYPE: PRT
<213> ORGANISM: Artificial Sequence
<220> FEATURE:
<223> OTHER INFORMATION: M1 Region

<400> SEQUENCE: 84

Ala Ala Thr Val Ser His Thr Thr His His Ala
1               5                   10

<210> SEQ ID NO 85
<211> LENGTH: 11
<212> TYPE: PRT
<213> ORGANISM: Artificial Sequence
<220> FEATURE:
<223> OTHER INFORMATION: M1 Region

<400> SEQUENCE: 85

Ala Ala Ala Val Ser His Thr Thr His His Ala
1               5                   10

<210> SEQ ID NO 86
<211> LENGTH: 10
<212> TYPE: PRT
<213> ORGANISM: Artificial Sequence
<220> FEATURE:
<223> OTHER INFORMATION: M1 Region

<400> SEQUENCE: 86

Ala Ala Val Ser His Thr Thr His His Ala
1               5                   10

<210> SEQ ID NO 87
<211> LENGTH: 12
<212> TYPE: PRT
<213> ORGANISM: Artificial Sequence
<220> FEATURE:
<223> OTHER INFORMATION: M1 Region

<400> SEQUENCE: 87

Ala Ala Ala Thr Val Ser His Thr Thr His His Ala
1               5                   10
```

```
<210> SEQ ID NO 88
<211> LENGTH: 9
<212> TYPE: PRT
<213> ORGANISM: Artificial Sequence
<220> FEATURE:
<223> OTHER INFORMATION: M1 Region

<400> SEQUENCE: 88

Ala Val Ser His Thr Thr His His Ala
1               5

<210> SEQ ID NO 89
<211> LENGTH: 15
<212> TYPE: PRT
<213> ORGANISM: Artificial Sequence
<220> FEATURE:
<223> OTHER INFORMATION: AviTag

<400> SEQUENCE: 89

Gly Leu Asn Asp Ile Phe Glu Ala Gln Lys Ile Glu Trp His Glu
1               5                   10                  15

<210> SEQ ID NO 90
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 90
atgtcctcca aaaaatctgg ttcatattcc ggctctaaag gcagtaaacg tcgtatctta      60

<210> SEQ ID NO 91
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 91
tcctccaaaa aatctggttc atattccggc tctaaaggca gtaaacgtcg tatctta         57

<210> SEQ ID NO 92
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 92
cactcctcct actggtacgc cttcaacaac aagacc                                36

<210> SEQ ID NO 93
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 93
gactccccgc acaccgagct gccg                                             24

<210> SEQ ID NO 94
<211> LENGTH: 21
<212> TYPE: PRT
<213> ORGANISM: Artificial Sequence
```

```
<220> FEATURE:
<223> OTHER INFORMATION: Synthetic polypeptide

<400> SEQUENCE: 94

Gly Met Ser Ser Lys Lys Ser Gly Ser Tyr Ser Gly Ser Lys Gly Ser
1               5                   10                  15

Lys Arg Arg Ile Leu
            20
```